United States Patent
Xu et al.

(10) Patent No.: US 10,808,043 B2
(45) Date of Patent: Oct. 20, 2020

(54) BISPECIFIC ANTIBODY OR ANTIBODY MIXTURE WITH COMMON LIGHT CHAINS

(71) Applicant: JIANGSU ALPHAMAB BIOPHARMACEUTICALS CO., LTD., Suzhou, Jiangsu (CN)

(72) Inventors: Ting Xu, Jiangsu (CN); Tao Xu, Jiangsu (CN); Xiaoxiao Wang, Jiangsu (CN); Qian Li, Jiangsu (CN); Minjie Pang, Jiangsu (CN); Huimin Zhang, Jiangsu (CN); Li Han, Jiangsu (CN); Qingqing Zhang, Jiangsu (CN)

(73) Assignee: Jiangsu Alphamab Biopharmaceuticals Co., Ltd., Suzhou, Jiangsu (CN)

( * ) Notice: Subject to any disclaimer, the term of this patent is extended or adjusted under 35 U.S.C. 154(b) by 58 days.

(21) Appl. No.: 15/541,921

(22) PCT Filed: Jan. 8, 2016

(86) PCT No.: PCT/CN2016/070447
§ 371 (c)(1),
(2) Date: Jul. 6, 2017

(87) PCT Pub. No.: WO2016/110267
PCT Pub. Date: Jul. 14, 2016

(65) Prior Publication Data
US 2019/0031782 A1    Jan. 31, 2019

(30) Foreign Application Priority Data
Jan. 8, 2015  (CN) .......................... 2015 1 0008045

(51) Int. Cl.
| | |
|---|---|
| *C07K 16/32* | (2006.01) |
| *A61P 35/00* | (2006.01) |
| *C07K 16/28* | (2006.01) |
| *C07K 16/30* | (2006.01) |
| *A61K 39/395* | (2006.01) |
| *C07K 16/46* | (2006.01) |
| *C12N 15/63* | (2006.01) |
| *C07K 14/71* | (2006.01) |
| *G01N 33/577* | (2006.01) |
| *A61K 39/00* | (2006.01) |

(52) U.S. Cl.
CPC .......... *C07K 16/468* (2013.01); *A61P 35/00* (2018.01); *C07K 14/71* (2013.01); *C07K 16/32* (2013.01); *C12N 15/63* (2013.01); *G01N 33/577* (2013.01); *A61K 39/395* (2013.01); *A61K 2039/505* (2013.01); *A61K 2039/507* (2013.01); *C07K 16/28* (2013.01); *C07K 2317/31* (2013.01); *C07K 2317/515* (2013.01); *C07K 2317/52* (2013.01); *C07K 2317/565* (2013.01); *C07K 2317/73* (2013.01); *C07K 2317/94* (2013.01)

(58) Field of Classification Search
CPC .. C07K 16/32; C07K 16/468; C07K 2317/31; C07K 2317/515; C07K 2317/52; C07K 2317/565; C07K 2317/73; C07K 2317/94; A61K 2039/505; A61K 2039/507
See application file for complete search history.

(56) References Cited

U.S. PATENT DOCUMENTS

2017/0029529 A1* 2/2017 Croasdale .............. C07K 16/32

FOREIGN PATENT DOCUMENTS

| CN | 1668636 A | 9/2005 | |
|---|---|---|---|
| CN | 103796678 A | 5/2014 | |
| JP | 2006-515503 | 6/2006 | |
| JP | 2012-515540 | 7/2012 | |
| JP | 2017-501706 | 1/2017 | |
| WO | 2004009618 | 1/2004 | |
| WO | 2010084197 | 7/2010 | |
| WO | WO-2012143523 A1 * | 10/2012 | ......... C07K 16/1063 |
| WO | 2015091738 | 6/2015 | |

OTHER PUBLICATIONS

Merchant et al., Nature Biotechnology, 1998. vol. 16, pp. 677-681.*
Li et al., Cancer Res: 2013, 73(21): 6471-83.*
Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*

(Continued)

*Primary Examiner* — Hong Sang

(74) *Attorney, Agent, or Firm* — Honigman LLP; Thomas A. Wootton, Esq.; Jonathan P. O'Brien

(57) ABSTRACT

The present application provides a bispecific antibody or an antibody mixture with common light chains and a preparation method therefor. the present application also provides a nucleic acid molecule encoding the antibody or the mixture, a recombinant vector and a recombinant cell comprising the nucleic acid molecule, as well as a detection and quantitation method for the antibody or the mixture.

2 Claims, 15 Drawing Sheets
Specification includes a Sequence Listing.

(56) References Cited

OTHER PUBLICATIONS

Lin, Guigao, "Identification of natural bispecific antibody against hepatitis C virus NS3 and NS5 proteins C patients and the study of producing mechanism of the NS3/NS5 bispecific antibody", Medicine & Public Health, China Doctoral Dissertations Full-Text Database, Feb. 15, 2014, No. 2, abstract.
Janet Jackman et al;Development of a Two-part Strategy to Identify a Therapeutic Human Bispecific Antibody That Inhibits IgE Receptor Signaling;The Journal of Biological Chemistry; vol. 285, No. 27;Jul. 2, 2010;pp. 20850-20859.
Bohua Li et al;Bispecific Antibody to ErbB2 Overcomes Trastuzumab Resistance through Comprehensive Blockade of ErbB2 Heterodimerization;Cancer Research, AACR, US Philadelphia, PA;vol. 73,No. 21 ;Nov. 1, 2013; pp. 6471-6483.
Matthew C. Franklin et al;Insights into ErbB signaling from the structure of the ErbB2-pertuzumab complex;Cancer Cell;Cell Press,US;vol. 5,No. 4;Apr. 1, 2004;pp. 317-328.

* cited by examiner a b

SEQUENCE LISTING

```
<160> NUMBER OF SEQ ID NOS: 28

<210> SEQ ID NO 1
<211> LENGTH: 214
<212> TYPE: PRT
<213> ORGANISM: Artificial Sequence
<220> FEATURE:
<223> OTHER INFORMATION: Synthetic peptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 2
<211> LENGTH: 214
<212> TYPE: PRT
<213> ORGANISM: Artificial Sequence
<220> FEATURE:
<223> OTHER INFORMATION: Synthetic peptide

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Ile Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 214
<212> TYPE: PRT
<213> ORGANISM: Artificial Sequence
<220> FEATURE:
<223> OTHER INFORMATION: Synthetic peptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 214
<212> TYPE: PRT
<213> ORGANISM: Artificial Sequence
<220> FEATURE:
<223> OTHER INFORMATION: Synthetic peptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ile Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60
```

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 5
<211> LENGTH: 214
<212> TYPE: PRT
<213> ORGANISM: Artificial Sequence
<220> FEATURE:
<223> OTHER INFORMATION: Synthetic peptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 6
<211> LENGTH: 214
<212> TYPE: PRT
<213> ORGANISM: Artificial Sequence
<220> FEATURE:
<223> OTHER INFORMATION: Synthetic peptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 7
gacatccaga tgacccagag ccccagcagc ctgagcgcca gcgtgggcga ccgcgtgacc    60
atcacctgcc gcgccagcca ggacgtgaac actgccgttg catggtacca gcagaagccc   120
ggcaaggccc ccaagctgct gatctacagc gccagcttcc tgtacagcgg cgtgcccagc   180
cgcttcagcg gcagccgcag cggcaccgac ttcaccctga ccatcagcag cctgcagccc   240
gaggacttcg ccacctacta ctgccagcag cactatacta ctcctccaac attcggccag   300
ggcaccaagg tggagatcaa agcgcaccgt gccgccccca gcgtgttcat cttccccccc   360
agcgacgagc agctcaagag cggcaccgcc agcgtggtgt gcctgctgaa caacttctac   420

```
ccccgcgagg ccaaggtgca gtggaaggtg acaacgccc tgcagagcgg caacagccag      480
gagagcgtga ccgagcagga cagcaaggac agcacctaca gcctgagcag cacccctgacc    540 ctgagcaagg ccgactacga aagcacaag gtgtacgcct gcgaggtgac ccaccagggc     600
ctgagcagcc ccgtgaccaa gagcttcaac cgcggcgagt gc                        642
```

<210> SEQ ID NO 8
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 8

```
gacatccaga tgacccagag ccccagcagc ctgagcgcca gcgtgggcga ccgcgtgacc      60
atcacctgcc gcgccagcca ggacgtgaac attgccgttg catggtacca gcagaagccc     120
ggcaaggccc ccaagctgct gatctacagc gccagcttcc tgtacagcgg cgtgcccagc     180
cgcttcagcg gcagccgcag cggcaccgac ttcaccctga ccatcagcag cctgcagccc     240
gaggacttcg ccacctacta ctgccagcag cactatacta ctcctccaac attcggccag     300
ggcaccaagg tggagatcaa gcgcaccgtg gccgccccca gcgtgttcat cttcccccc     360 agcgacgagc agctcaagag cggcaccgcc agcgtggtgt gcctgctgaa caacttctac     420
ccccgcgagg ccaaggtgca gtggaaggtg acaacgccc tgcagagcgg caacagccag     480
gagagcgtga ccgagcagga cagcaaggac agcacctaca gcctgagcag cacccctgacc   540 ctgagcaagg ccgactacga aagcacaag gtgtacgcct gcgaggtgac ccaccagggc     600
ctgagcagcc ccgtgaccaa gagcttcaac cgcggcgagt gc                        642
```

<210> SEQ ID NO 9
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 9

```
gacatccaga tgacccagag ccccagcagc ctgagcgcca gcgtgggcga ccgcgtgacc      60
atcacctgcc gcgccagcca ggacgtgaac actgccgttg catggtacca gcagaagccc     120
ggcaaggccc ccaagctgct gatctacagc gccagcttcc tgtacagcgg cgtgcccagc     180
cgcttcagcg gcagccgcag cggcaccgac ttcaccctga ccatcagcag cctgcagccc     240
gaggacttcg ccacctacta ctgccagcag cactatactt atcctccaac attcggccag     300
ggcaccaagg tggagatcaa gcgcaccgtg gccgccccca gcgtgttcat cttcccccc     360 agcgacgagc agctcaagag cggcaccgcc agcgtggtgt gcctgctgaa caacttctac     420
ccccgcgagg ccaaggtgca gtggaaggtg acaacgccc tgcagagcgg caacagccag     480
gagagcgtga ccgagcagga cagcaaggac agcacctaca gcctgagcag cacccctgacc   540 ctgagcaagg ccgactacga aagcacaag gtgtacgcct gcgaggtgac ccaccagggc     600
ctgagcagcc ccgtgaccaa gagcttcaac cgcggcgagt gc                        642
```

<210> SEQ ID NO 10
<211> LENGTH: 642
<212> TYPE: DNA
<213> ORGANISM: Artificial Sequence
<220> FEATURE:

<223> OTHER INFORMATION: Synthetic oligonucleotide

<400> SEQUENCE: 10

```
gacatccaga tgacccagag ccccagcagc ctgagcgcca gcgtgggcga ccgcgtgacc        60
atcacctgcc gcgccagcca ggacgtgaac attgccgttg catggtacca gcagaagccc       120
ggcaaggccc ccaagctgct gatctacagc gccagcttcc tgtacagcgg cgtgcccagc       180
cgcttcagcg gcagccgcag cggcaccgac ttcaccctga ccatcagcag cctgcagccc       240
gaggacttcg ccacctacta ctgccagcag cactatactt atcctccaac attcggccag       300
ggcaccaagg tggagatcaa gcgcaccgtg gccgccccca gcgtgttcat cttcccccc        360
agcgacgagc agctcaagag cggcaccgcc agcgtggtgt gcctgctgaa caacttctac       420
ccccgcgagg ccaaggtgca gtggaaggtg gacaacgccc tgcagagcgg caacagccag       480
gagagcgtga ccgagcagga cagcaaggac agcacctaca gcctgagcag caccctgacc       540
ctgagcaagg ccgactacga gaagcacaag gtgtacgcct gcgaggtgac ccaccagggc       600
ctgagcagcc ccgtgaccaa gagcttcaac cgcggcgagt gc                           642
```

<210> SEQ ID NO 11
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 11

```
gacatccaga tgacccagag ccccagcagc ctgagcgcca gcgtgggcga ccgcgtgacc        60
atcacctgca aggccagcca ggacgtgagc atcggcgtgg cctggtacca gcagaagccc       120
ggcaaggccc ccaagctgct gatctacagc gccagctacc gctacaccgg cgtgcccagc       180
cgcttcagcg gcagcggcag cggcaccgac ttcaccctga ccatcagcag cctgcagccc       240
gaggacttcg ccacctacta ctgccagcag tactacatct accccacac cttcggccag        300
ggcaccaagg tggagatcaa gcgcaccgtg gccgccccca gcgtgttcat cttcccccc        360
agcgacgagc agctcaagag cggcaccgcc agcgtggtgt gcctgctgaa caacttctac       420
ccccgcgagg ccaaggtgca gtggaaggtg gacaacgccc tgcagagcgg caacagccag       480
gagagcgtga ccgagcagga cagcaaggac agcacctaca gcctgagcag caccctgacc       540
ctgagcaagg ccgactacga gaagcacaag gtgtacgcct gcgaggtgac ccaccagggc       600
ctgagcagcc ccgtgaccaa gagcttcaac cgcggcgagt gc                           642
```

<210> SEQ ID NO 12
<211> LENGTH: 642
<212> TYPE: DNA
<213> ORGANISM: Artificial Sequence
<220> FEATURE:
<223> OTHER INFORMATION: Synthetic oligonucleotide

<400> SEQUENCE: 12

```
gacatccaga tgacccagag ccccagcagc ctgagcgcca gcgtgggcga ccgcgtgacc        60
atcacctgca aggccagcca ggacgtgagc atcggcgtgg cctggtacca gcagaagccc       120
ggcaaggccc ccaagctgct gatctacagc gccagctacc gctacaccgg cgtgcccagc       180
cgcttcagcg gcagcggcag cggcaccgac ttcaccctga ccatcagcag cctgcagccc       240
gaggacttcg ccacctacta ctgccagcag tactacatca cccctacac cttcggccag        300
ggcaccaagg tggagatcaa gcgcaccgtg gccgccccca gcgtgttcat cttccccccc      360
```

```
agcgacgagc agctcaagag cggcaccgcc agcgtggtgt gcctgctgaa caacttctac    420
ccccgcgagg ccaaggtgca gtggaaggtg gacaacgccc tgcagagcgg caacagccag    480
gagagcgtga ccgagcagga cagcaaggac agcacctaca gcctgagcag caccctgacc    540
ctgagcaagg ccgactacga gaagcacaag gtgtacgcct gcgaggtgac ccaccagggc    600
ctgagcagcc ccgtgaccaa gagcttcaac cgcggcgagt gc                      642
```

```
<210> SEQ ID NO 13
<211> LENGTH: 630
<212> TYPE: PRT
<213> ORGANISM: Artificial Sequence
<220> FEATURE:
<223> OTHER INFORMATION: Synthetic peptide

<400> SEQUENCE: 13
```

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ala
        275                 280                 285

Cys Thr Leu Val Cys Pro Leu Ala Asn Gln Glu Val Thr Ala Glu Asp
    290                 295                 300

Gly Thr Gln Arg Cys Glu Lys Cys Ser Lys Pro Cys Ala Arg Val Cys
```

```
            305                 310                 315                 320

Tyr Gly Leu Gly Met Glu His Leu Arg Glu Val Arg Ala Val Thr Ser
                        325                 330                 335

Ala Asn Ile Gln Glu Phe Ala Gly Cys Lys Lys Ile Phe Gly Ser Leu
                        340                 345                 350

Ala Phe Leu Pro Glu Ser Phe Asp Gly Asp Pro Ala Ser Asn Thr Ala
                        355                 360                 365

Pro Leu Gln Pro Glu Gln Leu Gln Val Phe Glu Thr Leu Glu Glu Ile
                        370                 375                 380

Thr Gly Tyr Leu Tyr Ile Ser Ala Trp Pro Asp Ser Leu Pro Asp Leu
        385                 390                 395                 400

Ser Val Phe Gln Asn Leu Gln Val Ile Arg Gly Arg Ile Leu His Asn
                        405                 410                 415

Gly Ala Tyr Ser Leu Thr Leu Gln Gly Leu Gly Ile Ser Trp Leu Gly
                        420                 425                 430

Leu Arg Ser Leu Arg Glu Leu Gly Ser Gly Leu Ala Leu Ile His His
                        435                 440                 445

Asn Thr His Leu Cys Phe Val His Thr Val Pro Trp Asp Gln Leu Phe
                        450                 455                 460

Arg Asn Pro His Gln Ala Leu Leu His Thr Ala Asn Arg Pro Glu Asp
        465                 470                 475                 480

Glu Cys Val Gly Glu Gly Leu Ala Cys His Gln Leu Cys Ala Arg Gly
                        485                 490                 495

His Cys Trp Gly Pro Gly Pro Thr Gln Cys Val Asn Cys Ser Gln Phe
                        500                 505                 510

Leu Arg Gly Gln Glu Cys Val Glu Glu Cys Arg Val Leu Gln Gly Leu
                        515                 520                 525

Pro Arg Glu Tyr Val Asn Ala Arg His Cys Leu Pro Cys His Pro Glu
                        530                 535                 540

Cys Gln Pro Gln Asn Gly Ser Val Thr Cys Phe Gly Pro Glu Ala Asp
        545                 550                 555                 560

Gln Cys Val Ala Cys Ala His Tyr Lys Asp Pro Pro Phe Cys Val Ala
                        565                 570                 575

Arg Cys Pro Ser Gly Val Lys Pro Asp Leu Ser Tyr Met Pro Ile Trp
                        580                 585                 590

Lys Phe Pro Asp Glu Glu Gly Ala Cys Gln Pro Cys Pro Ile Asn Cys
                        595                 600                 605

Thr His Ser Cys Val Asp Leu Asp Asp Lys Gly Cys Pro Ala Glu Gln
                        610                 615                 620

Arg Ala Ser Pro Leu Thr
        625                 630

<210> SEQ ID NO 14
<211> LENGTH: 630
<212> TYPE: PRT
<213> ORGANISM: Artificial Sequence
<220> FEATURE:
<223> OTHER INFORMATION: Synthetic peptide

<400> SEQUENCE: 14

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
```

-continued

```
                35                  40                  45
Leu Ser Phe Leu Gln Asp Ile Gln Glu Val Gln Gly Tyr Val Leu Ile
 50                  55                  60
Ala His Asn Gln Val Arg Gln Val Pro Leu Gln Arg Leu Arg Ile Val
 65                  70                  75                  80
Arg Gly Thr Gln Leu Phe Glu Asp Asn Tyr Ala Leu Ala Val Leu Asp
                 85                  90                  95
Asn Gly Asp Pro Leu Asn Asn Thr Thr Pro Val Thr Gly Ala Ser Pro
                100                 105                 110
Gly Gly Leu Arg Glu Leu Gln Leu Arg Ser Leu Thr Glu Ile Leu Lys
                115                 120                 125
Gly Gly Val Leu Ile Gln Arg Asn Pro Gln Leu Cys Tyr Gln Asp Thr
                130                 135                 140
Ile Leu Trp Lys Asp Ile Phe His Lys Asn Asn Gln Leu Ala Leu Thr
145                 150                 155                 160
Leu Ile Asp Thr Asn Arg Ser Arg Ala Cys His Pro Cys Ser Pro Met
                165                 170                 175
Cys Lys Gly Ser Arg Cys Trp Gly Glu Ser Ser Glu Asp Cys Gln Ser
                180                 185                 190
Leu Thr Arg Thr Val Cys Ala Gly Gly Cys Ala Arg Cys Lys Gly Pro
                195                 200                 205
Leu Pro Thr Asp Cys Cys His Glu Gln Cys Ala Ala Gly Cys Thr Gly
                210                 215                 220
Pro Lys His Ser Asp Cys Leu Ala Cys Leu His Phe Asn His Ser Gly
225                 230                 235                 240
Ile Cys Glu Leu His Cys Pro Ala Leu Val Thr Tyr Asn Thr Asp Thr
                245                 250                 255
Phe Glu Ser Met Pro Asn Pro Glu Gly Arg Tyr Thr Phe Gly Ala Ser
                260                 265                 270
Cys Val Thr Ala Cys Pro Tyr Asn Tyr Leu Ser Thr Asp Val Gly Ser
                275                 280                 285
Cys Thr Leu Val Cys Pro Leu His Asn Gln Glu Val Thr Ala Glu Asp
                290                 295                 300
Gly Thr Gln Arg Cys Glu Lys Cys Ser Lys Pro Cys Ala Arg Val Cys
305                 310                 315                 320
Tyr Gly Leu Gly Met Glu His Leu Arg Glu Val Arg Ala Val Thr Ser
                325                 330                 335
Ala Asn Ile Gln Glu Phe Ala Gly Cys Lys Lys Ile Phe Gly Ser Leu
                340                 345                 350
Ala Phe Leu Pro Glu Ser Phe Asp Gly Asp Pro Ala Ser Asn Thr Ala
                355                 360                 365
Pro Leu Gln Pro Glu Gln Leu Gln Val Phe Glu Thr Leu Glu Glu Ile
                370                 375                 380
Thr Gly Tyr Leu Tyr Ile Ser Ala Trp Pro Asp Ser Leu Pro Asp Leu
385                 390                 395                 400
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
                420                 425                 430
Leu Arg Ser Leu Arg Glu Leu Gly Ser Gly Leu Ala Leu Ile His His
                435                 440                 445
Asn Thr His Leu Cys Phe Val His Thr Val Pro Trp Asp Gln Leu Phe
                450                 455                 460
```

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Ala Ala Asp
545                 550                 555                 560

Gln Cys Val Ala Cys Ala His Tyr Lys Asp Pro Ala Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr
625                 630

<210> SEQ ID NO 15
<211> LENGTH: 630
<212> TYPE: PRT
<213> ORGANISM: Artificial Sequence
<220> FEATURE:
<223> OTHER INFORMATION: Synthetic peptide

<400> SEQUENCE: 15

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

```
Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

Cys Val Thr Ala Cys Pro Tyr Asn Tyr Leu Ser Thr Asp Val Gly Ser
            275                 280                 285

Cys Thr Leu Val Cys Pro Leu His Asn Gln Glu Val Thr Ala Glu Asp
        290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Ala Ala Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605
```

Thr His Ser Cys Val Asp Leu Asp Asp Lys Gly Cys Pro Ala Glu Gln
610                 615                 620

Arg Ala Ser Pro Leu Thr
625             630

<210> SEQ ID NO 16
<211> LENGTH: 1350
<212> TYPE: DNA
<213> ORGANISM: Artificial Sequence
<220> FEATURE:
<223> OTHER INFORMATION: Synthetic oligonucleotide

<400> SEQUENCE: 16

```
gaggtgcagc tcgtggagag cggcggcggc ctggtgcagc ccggcggcag cctgcgcctg      60
agctgcgccg ccagcggctt caacatcaag gacacctaca tccactgggt gcgccaggcc     120
cccggcaagg gcctggagtg ggtggcccgc atctacccca ccaacggcta cacccgctac     180
gccgacagcg tgaagggccg cttcaccatc agcgccgaca ccagcaagaa caccgcctac     240
ctgcagatga acagcctgcg cgccgaggac accgccgtgt actactgcag ccgctggggc     300
ggcgacggct tctacgccat ggactactgg ggccagggca ccctggtgac cgtgagcagc     360
gccagcacca agggccccag cgtgttcccc ctggccccca gcagcaagag caccagcggc     420
ggcaccgccg ccctgggctg cctggtgaag gactacttcc ccgagcccgt gaccgtgagc     480
tggaacagcg gcgccctgac cagcggcgtg cacaccttcc ccgccgtgct gcagagcagc     540
ggcctgtaca gcctgagcag cgtggtgacc gtgcccagca gcagcctggg cacccagacc     600
tacatctgca acgtgaacca caagcccagc aacaccaagg tggacaagaa ggtggagccc     660
aagagctgcg acaagaccca cacctgcccc cctgccccg ccccgagct gctgggcggc      720
cccagcgtgt tcctgttccc ccccaagccc aaggacaccc tgatgatcag ccgcaccccc     780
gaggtgacct gcgtggtggt ggacgtgagc cacgaggacc ccgaggtgaa gttcaactgg     840
tacgtggacg gcgtggaggt gcacaacgcc aagaccaagc ccgcgagga gcagtacaac     900
agcacctacc gcgtggtgag cgtgctgacc gtgctgcacc aggactggct gaacggcaag     960
gagtacaagt gcaaggtgag caacaaggcc ctgcccgccc ccatcgagaa gaccatcagc    1020
aaggccaagg gccagccccg cgagccccag gtgtacaccc tgccccccag ccgcgaggag    1080
atgaccaaga accaggtgag cctgacctgc ctggtgaagg gcttctaccc cagcgacatc    1140
gccgtggagt gggagagcaa cggccagccc gagaacaact acaagaccac ccccccgtg    1200
ctggacagcg acggcagctt cttcctgtac agcaagctga ccgtggacaa gagccgctgg    1260
cagcagggca acgtgttctc gtgcagcgtg atgcacgagg ccctgcacaa ccactacacc    1320
cagaagagcc tgagcctgag ccccggcaag                                     1350
```

<210> SEQ ID NO 17
<211> LENGTH: 1347
<212> TYPE: DNA
<213> ORGANISM: Artificial Sequence
<220> FEATURE:
<223> OTHER INFORMATION: Synthetic oligonucleotide

<400> SEQUENCE: 17

```
gaggtgcagc tcgtggagag cggcggcggc ctggtgcagc ccggcggcag cctgcgcctg      60
agctgcgccg ccagcggctt caccttcacc gactacacca tggactgggt gcgccaggcc     120
cccggcaagg gcctggagtg ggtggccgac gtgaacccca cagcggcgg cagcatctac     180
aaccagcgct tcaagggccg cttcacccttg agcgtggacc gcagcaagaa cacccttgtac     240
```

-continued

```
ctgcagatga acagcctgcg cgccgaggac accgccgtgt actactgcgc ccgcaacctg    300
ggccccagct tctacttcga ctactggggc cagggcaccc tggtgaccgt gagcagcgcc    360
agcaccaagg gccccagcgt gttccccctg gccccagca gcaagagcac cagcggcggc    420
accgccgccc tgggctgcct ggtgaaggac tacttccccg agcccgtgac cgtgagctgg    480
aacagcggcg ccctgaccag cggcgtgcac accttccccg ccgtgctgca gagcagcggc    540
ctgtacagcc tgagcagcgt ggtgaccgtg cccagcagca gcctgggcac ccagacctac    600
atctgcaacg tgaaccacaa gcccagcaac accaaggtgg acaagaaggt ggagcccaag    660
agctgcgaca gacccacac ctgccccccc tgccccgccc ccgagctgct gggcggcccc    720
agcgtgttcc tgttcccccc caagcccaag gacaccctga tgatcagccg cacccccgag    780
gtgacctgcg tggtggtgga cgtgagccac gaggaccccg aggtgaagtt caactggtac    840
gtggacggcg tggaggtgca caacgccaag accaagcccc gcgaggagca gtacaacagc    900
acctaccgcg tggtgagcgt gctgaccgtg ctgcaccagg actggctgaa cggcaaggag    960
tacaagtgca aggtgagcaa caaggccctg cccgccccca tcgagaagac catcagcaag    1020
gccaagggcc agccccgcga gccccaggtg tacaccctgc cccccagccg cgaggagatg    1080
accaagaacc aggtgagcct gacctgcctg gtgaagggct tctacccag cgacatcgcc    1140 gtggagtggg agagcaacgg ccagcccgag aacaactaca agaccaccc ccccgtgctg    1200 gacagcgacg gcagcttctt cctgtacagc aagctgaccg tggacaagag ccgctggcag    1260
cagggcaacg tgttctcgtg cagcgtgatg cacgaggccc tgcacaacca ctacacccag    1320
aagagcctga gcctgagccc cggcaag                                        1347
```

<210> SEQ ID NO 18
<211> LENGTH: 630
<212> TYPE: PRT
<213> ORGANISM: Artificial Sequence
<220> FEATURE:
<223> OTHER INFORMATION: Synthetic HER2-ECD

<400> SEQUENCE: 18

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160
```

```
Leu Ile Asp Thr Asn Arg Ser Arg Ala Cys His Pro Cys Ser Pro Met
            165                 170                 175

Cys Lys Gly Ser Arg Cys Trp Gly Glu Ser Ser Glu Asp Cys Gln Ser
        180                 185                 190

Leu Thr Arg Thr Val Cys Ala Gly Gly Cys Ala Arg Cys Lys Gly Pro
    195                 200                 205

Leu Pro Thr Asp Cys Cys His Glu Gln Cys Ala Ala Gly Cys Thr Gly
210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
```

```
                    580                 585                 590
Lys Phe Pro Asp Glu Glu Gly Ala Cys Gln Pro Cys Pro Ile Asn Cys
                595                 600                 605

Thr His Ser Cys Val Asp Leu Asp Asp Lys Gly Cys Pro Ala Glu Gln
            610                 615                 620

Arg Ala Ser Pro Leu Thr
625                 630

<210> SEQ ID NO 19
<211> LENGTH: 450
<212> TYPE: PRT
<213> ORGANISM: Artificial Sequence
<220> FEATURE:
<223> OTHER INFORMATION: Synthetic peptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                305                 310                 315                 320
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
                355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 20
<211> LENGTH: 449
<212> TYPE: PRT
<213> ORGANISM: Artificial Sequence
<220> FEATURE:
<223> OTHER INFORMATION: Synthetic peptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Thr Met Asp Trp Val Arg Gln Ala Pro Gly Lys Gly Leu Glu Trp Val
                35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
```

-continued

```
                210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 21
<211> LENGTH: 450
<212> TYPE: PRT
<213> ORGANISM: Artificial Sequence
<220> FEATURE:
<223> OTHER INFORMATION: Synthetic peptide

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125
```

-continued

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 449
<212> TYPE: PRT
<213> ORGANISM: Artificial Sequence
<220> FEATURE:
<223> OTHER INFORMATION: Synthetic peptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Asp Thr Thr Pro Pro Val Leu
385                 390                 395                 400

Lys Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 23
<211> LENGTH: 120
<212> TYPE: PRT
<213> ORGANISM: Artificial Sequence
<220> FEATURE:
<223> OTHER INFORMATION: Synthetic peptide

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 24
<211> LENGTH: 119
<212> TYPE: PRT
<213> ORGANISM: Artificial Sequence
<220> FEATURE:
<223> OTHER INFORMATION: Synthetic peptide

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 25
<211> LENGTH: 227
<212> TYPE: PRT
<213> ORGANISM: Artificial Sequence
<220> FEATURE:
<223> OTHER INFORMATION: Synthetic peptide

<400> SEQUENCE: 25

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 26
<211> LENGTH: 227
<212> TYPE: PRT
<213> ORGANISM: Artificial Sequence
<220> FEATURE:
<223> OTHER INFORMATION: Synthetic peptide

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225

<210> SEQ ID NO 27
<211> LENGTH: 227
<212> TYPE: PRT
<213> ORGANISM: Artificial Sequence
<220> FEATURE:
<223> OTHER INFORMATION: Synthetic peptide

<400> SEQUENCE: 27

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225

<210> SEQ ID NO 28

```
<211> LENGTH: 227
<212> TYPE: PRT
<213> ORGANISM: Artificial Sequence
<220> FEATURE:
<223> OTHER INFORMATION: Synthetic peptide

<400> SEQUENCE: 28

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Lys Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

BISPECIFIC ANTIBODY OR ANTIBODY MIXTURE WITH COMMON LIGHT CHAINS

TECHNICAL FIELD

The present invention relates to a bispecific antibody or an antibody mixture, and a preparation method of the bispecific antibody or the antibody mixture. The present invention also relates to a nucleic acid molecule encoding the bispecific antibody or the antibody mixture, a recombinant vector and a recombinant cell containing the nucleic acid molecule, and a detection and quantification method of the bispecific antibody or the antibody mixture.

BACKGROUND

The number of monoclonal antibody drugs being marketed rapidly increases during the recent 15 years, and has become a field of growth in the pharmaceutical industry. Since 1996, about 30 monoclonal antibody drugs have been approved in total, wherein the annual sale of 9 monoclonal antibody drugs is more than USD 1 billion. In 2010, the total sale of the monoclonal antibody drugs exceeds USD 30 billion, with an annual growth rate of more than 10%. Due to its strong target specificity, a monoclonal antibody can only inhibit a single target, while in many diseases (including tumor and autoimmune diseases), it is needed to inhibit multiple signal pathways to avoid compensation effects. For virus infection diseases, due to high mutation rate of virus, it is often needed to inhibit multiple antigen sites to prevent escape. Hence, there are several alternatives to solve this problem. One alternative is using a polyclonal antibody, or a heterodimer (such as a bispecific antibody) obtained by modifying an Fc fragment of the antibody, so that it will have activities against at least two different antigens or two different binding sites of the same antigen. Another alternative is using an antibody mixture, which may contain two or more antibodies against different antigen epitopes on the same target or against different targets.

A bispecific antibody (BsAbs) is an immunoglobulin molecule containing two different ligand binding sites. It comprises two different Fab sequences, instead of the same sequences for the two Fab arms of a classical antibody. Hence, two arms of the Y shaped antibody can bind to different antigen epitopes. Application of the bispecific antibody in cancer treatment has been reviewed in multiple documents (Carter 2001; Chames and Baty 2009; Chames and Baty 2009). One arm of BsAbs can be connected with a tumor cell surface related antigen and the other arm can trigger immune effector cells to further kill cells so as to kill tumor cells with the help of the immune system.

For the preparation of a bispecific antibody, as early as in the 1990s, Carter et al. modified some amino acids of a heavy chain of an antibody using a "knob into hole" model to successfully achieve the preparation of the bispecific antibody (Ridgway, Presta et al. 1996; Carter 2001). However, in their research, the ability of preventing formation of "hole to hole" homodimers were still insufficient, about 5% of homodimers was still observed. After that, this research group tried to further improve the content of heterodimers through methods such as random mutation-phage display, but the problem was not fundamentally solved.

The inventors of the present invention modified CH3 related amino acids of Fc based on a charged amino acid interaction network to weaken interactions of the domains between themselves (which facilitates formation of homodimers) and enhance the interactions between different domains (which facilitates formation of heterodimers), thereby successfully solving the problem of 5% remaining homodimers in the "knob into hole" model, and related methods have been described in a patent application (Publication No: CN102558355A).

In contrast to the heterodimer platform technology, development of an antibody mixture production platform is still in a relatively early stage, wherein much attention has been drawn to an antibody mixture technology from the Danish company Symphogen A/S. This technology first aims to obtain multiple antibodies against the same target by screening using an antibody screening platform, then constructing a cell strain for each antibody respectively, then mixing seed solutions cultured in different flasks, and finally gradually amplifying the reaction and optimizing the purification process to obtain a final product. Although by this method, multiple antibodies can be obtained directly from one recombinant production process by culturing a mixed population of multiple cells, this scheme still has some potential problems due to difficulties in controlling mixed cell populations and complexities related with subsequent scale-up.

The applicant of the present invention invents a method for producing a mixture comprising two or more homodimer proteins or antibodies in a single recombinant cell through mutating Fc portions to change direct interactions between Fc fragments. This method avoids potential difficulties in process control and scale-up brought about by mixed cell culture, and provides a more economic and effective approach for antibody mixture preparation and production. This scheme has also been described in an earlier patent application (Publication No: CN103388013A).

However, no matter which method discussed above is used, mismatching between light chains and heavy chains can still happen when a complete-antibody frame is utilized to prepare the bispecific antibody or antibody mixtures thereof, thereby affecting the activity of the antibody. Currently, a relatively mature method in the art is Crossmab developed by Roche (Genentech), that is, substituting light chain-heavy chain sequences in one Fab to prevent mismatching between this light chain sequence with light chain or heavy chain sequences of the other Fab (Patent Number US20090162359, US20120164726). Although this method may be used to solve most problems of heavy chain-light chain mismatching, yet new problems may be brought about due to modifications in heavy chain and light chain sequences, for example, dissociation of light chains, increase of multimers, and some influences on recognition of antigen epitopes for some Fab sequences.

HERCEPTIN® (also referred to as Trastuzumab), as a first therapeutic monoclonal antibody showing clinical effect in breast cancer, is an anti-human epidermal growth factor receptor 2(HER2) monoclonal antibody, which acts on HER2-Neu surface proteins of breast cancer cells to interfere with a biological process of cancer cells and finally kill the cancer cells. The proper patient population for HERCEPTIN® (trastuzumab) is that of breast cancer with HER2 overexpression (immunohistochemical 3+ or fluorescence in situ hybridization FISH positive), and this group approximately accounts for 20-30% of all breast cancer patients.

Pertuzumab is a recombinant monoclonal antibody, which binds to extracellular domain II of HER-2 receptor to inhibit formation of dimers and inhibit a receptor-mediated signal transduction (Agus D B, Gordon M S, Taylor C, et al. 2005). This may partially explain the reason for Pertuzumab monoclonal antibody to inhibit growth of HER-2 under-expression tumor, while Trastuzumab binds to an extracellular IV region of the HER-2 receptor, and formation of dimers does not involve the IV region. Hence, Trastuzumab is only effective for breast cancer patients with HER-2 overexpression. At present, a phase II clinical trial for the treatment of terminal stage breast cancer with HER-2 under-expression using Pertuzumab is undergoing. The research of Baselga (Baselga J, et al. 2007) et al. shows that the combination of Pertuzumab and HERCEPTIN® (trastuzumab) has anti-tumor activity for HER-2 positive breast cancer patients refractory to treatment. This result shows that Pertuzumab is efficacious for ⅕ of the patients (tumor is diminished or disappeared), and the status of another ⅕ of the patients were maintained stable for 6 months or longer. A result of a Phase III clinical trial for treating breast cancer with Pertuzumab shows that this drug can prolong progression-free survival of patients with ERBB2 positive metastatic breast cancer.

Presently, Roche announced a latest trial result. The trial was a Phase II therapy on the clinical effect for treating female breast cancer patients positive for the protooncogene human epidermal growth factor receptor 2 (HER2), using Pertuzumab and HERCEPTIN® (trastuzumab) in combination with a chemotherapy (docetaxel). The data shown by the Cancer Therapy & Research Center-American Association for Cancer Research (CTRC-AACR) in San Antonio Breast Cancer Seminar (SABCS) demonstrated that the complete remission rate (with a complete remission rate of 45.8% of cases) of breast tumor treated by administrating a combination of the two antibodies and docetaxel in preoperative neoadjuvant therapy is significantly enhanced by more than 50% as compared to that of the combination of HERCEPTIN® (trastuzumab) and docetaxel (complete remission rate of 29.0% of cases). Comparing to HERCEPTIN® (trastuzumab) and chemotherapy, Pertuzumab and combination of Pertuzumab with docetaxel would not cause side effects or significant increase of risks of heart diseases.

The present invention takes Pertuzumab and Trastuzumab as examples to prepare a bispecific antibody and an antibody mixture having the functions of both Pertuzumab and Trastuzumab, and based on this, developed a new method for preparing a bispecific antibody or an antibody mixture, wherein light chains and heavy chains can assemble correctly.

SUMMARY

Through repeated experimentation, the inventors of the present application surprisingly found that light chains originally present in two antibodies or antibody mixtures can be replaced with a common light chain so as to obtain a bispecific antibody or antibody mixture comprising the common light chain. In the bispecific antibody or antibody mixture comprising the common light chain, the light chains and the heavy chains are capable of assembling correctly. In addition, in comparison with the two original antibodies, the bispecific antibody has good binding activity, biological activity and stability, moreover, the bispecific antibody has better biological activity than the original antibodies.

A first aspect of the present application relates to a bispecific antibody or an antigen binding portion thereof, wherein the bispecific antibody or the antigen binding portion thereof has a common light chain, and wherein said common light chain refers to two light chains having the same sequence.

In one embodiment, heavy chains of the bispecific antibody or the antigen binding portion thereof are capable of correctly assembling with said light chains respectively under physiological conditions or during in vitro protein expression.

In one embodiment, the common light chain of the bispecific antibody or the antigen binding portion thereof is obtained by modifying two original monoclonal antibodies (known monoclonal antibodies), and the sequence of the common light chain is different from that of a light chain of at least one of the two original monoclonal antibodies. In one embodiment, the common light chain is the same as the light chain of one of the two original monoclonal antibodies, or is obtained via modification on the basis of the two original monoclonal antibodies (such as amino acid sequence modification), and the objective of the modification is to maintain affinity with the respective antigen or antigen epitope as much as possible. In one embodiment, the modification of amino acid sequence comprises mutation, deletion or addition of amino acids, for example, the mutation, deletion or addition of no more than 3 amino acids, preferably no more than 2 amino acids, and more preferably no more than 1 amino acid.

In one embodiment, an Fc fragment of a heavy chain of the bispecific antibody or the antigen binding portion thereof is modified to facilitate formation of a heterodimer protein.

In one embodiment, the two original monoclonal antibodies are Pertuzumab and Trastuzumab.

In one embodiment, the common light chain is capable of assembling with a heavy chain of Pertuzumab and a heavy chain of Trastuzumab, respectively.

In one embodiment, the common light chain is a light chain selected from a light chain of Pertuzumab or a light chain of trastuzumab, or a mutant thereof. In one embodiment, the heavy chains (comprising a variable region and a constant region) of the bispecific antibody or the antigen binding portion thereof can be the same as heavy chains of the two original monoclonal antibodies, or be modified to facilitate formation of the heterodimer protein; the modification, for example, is a modification in the heavy chain Fc fragment so as to facilitate formation of the heterodimer protein.

In one embodiment, a sequence of a variable region of the common light chain comprises a sequence selected from those as set forth in amino acid positions 1-107 of SEQ ID NO: 1-SEQ ID NO: 6.

In one embodiment, a sequence of a light chain constant region comprises a sequence selected from those as set forth in amino acid positions 108-214 of SEQ ID NO: 1.

In one embodiment, heavy chain variable regions thereof are a heavy chain variable region of Pertuzumab and a heavy chain variable region of Trastuzumab, respectively.

In one embodiment, the heavy chain variable regions comprise sequences as set forth in SEQ ID NO: 23 and SEQ ID NO: 24, respectively.

In one embodiment, Fc fragments sequences of the heavy chain comprise sequences as set forth in SEQ ID NO: 25 and SEQ ID NO: 26, respectively.

In one embodiment, two heavy chains thereof comprise a sequence as set forth in SEQ ID NO: 19 and SEQ ID NO: 20, respectively.

A second aspect of the present application relates to a mixture of antibodies or antigen binding portions thereof, wherein said antibodies or antigen binding portions thereof are capable of being produced correctly in one cell. The mixture comprises at least two antibodies or antigen binding portion thereof, and the antibodies or antigen binding portion thereof have a common light chain, and the common light chain refers to two light chain variable regions having the same sequence.

In one embodiment, heavy chains of the antibody or the antigen binding portion thereof are capable of correctly assembling with the light chains respectively under the physiological conditions or during in vitro protein expression.

In one embodiment, the common light chain of the bispecific antibody or antigen binding portion thereof is obtained by modifying the two original monoclonal antibodies (known monoclonal antibodies), the sequence of the common light chain is different from that of the light chain of at least one of the two original monoclonal antibodies. In one embodiment, the common light chain is the same as the light chain of one of the two original monoclonal antibodies, or is obtained via modification (such as amino acid modification) on the basis of the two original monoclonal antibodies, the objective of the modification is to maintain affinity with the respective antigen or antigen epitope as much as possible. In one embodiment, the amino acid modification comprises mutation, deletion or addition of amino acid, for example, mutation, deletion or addition of no more than 3 amino acids, preferably no more than 2 amino acids, more preferably on more than 1 amino acid.

In one embodiment, the heavy chains of the bispecific antibody or antigen binding portion thereof are derived from the two original monoclonal antibodies, the sequence of the heavy chain variable region and/or CH1 domain of the bispecific antibody or antigen binding portion thereof is the same as that of the original monoclonal antibodies.

In one embodiment, the heavy chain (including a variable region and a constant region) of the bispecific antibody or antigen binding portion thereof may be the same as heavy chains of the two original monoclonal antibodies, or may be modified to facilitate formation of the homodimer protein; the modification, for example, is a modification of heavy chain Fc fragment to facilitate formation of the homodimer protein.

In one embodiment, the two original monoclonal antibodies are Pertuzumab and Trastuzumab.

In one embodiment, the common light chain is capable of assembling with a heavy chain of Pertuzumab and a heavy chain of Trastuzumab, respectively.

In one embodiment, the common light chain is selected from a light chain of Pertuzumab, a light chain of Trastuzumab or a mutant thereof.

In one embodiment, a sequence of a variable region of the common light chain comprises a sequence selected from sequences as set forth in amino acid positions 1-107 of SEQ ID NO: 1-SEQ ID NO: 6.

In one embodiment, a sequence of a constant region of the light chain comprises a sequence selected from sequences as set forth in amino acid positions 108-214 of SEQ ID NO: 1.

In one embodiment, heavy chain variable regions of the antibody or antigen binding portion thereof are a heavy chain variable region of Pertuzumab and a heavy chain variable region of Trastuzumab, respectively.

In one embodiment, a sequence of a variable region of the two heavy chains comprises a sequence as set forth in in SEQ ID NO: 23 and SEQ ID NO: 24, respectively.

In one embodiment, Fc fragment sequences of the heavy chains of the antibody or antigen binding portion thereof comprise sequences as set forth in SEQ ID NO: 27 and SEQ ID NO: 28, respectively.

In one embodiment, sequences of the heavy chains of the antibody or antigen binding portion thereof comprise sequences as set forth in SEQ ID NO: 21 and SEQ ID NO: 22, respectively.

A third aspect of the present application relates to a variant protein of a HER2 protein extracellular domain, wherein, when comparing to a sequence of a wild type HER2 protein extracellular domain, the variant protein comprises mutations selected from the group consisting of:

1) a mutation of glutamic acid at position 558 and a mutation of phenylalanine at position 573; and 2) a mutation of serine at position 288 and a mutation of histidine at position 296.

In one embodiment, a mutation from glutamic acid at position 558 to alanine.

In one embodiment, a mutation from phenylalanine at position 573 to alanine.

In one embodiment, a mutation from serine at position 288 to alanine.

In one embodiment, a mutation from histidine at position 296 to alanine.

In one embodiment, the HER2 variant protein comprises an amino acid sequence selected from the amino acid sequences as set forth in SEQ ID NO:13, SEQ ID NO: 14 and SEQ ID NO: 15.

In one embodiment, a sequence of the wild type HER2 protein extracellular domain is as set forth in SEQ ID NO: 18.

A fourth aspect of the present application relates to a nucleic acid molecule, encoding the bispecific antibody or antigen binding portion thereof according to any one of the first aspect of the present application, or the bispecific antibodies or antigen binding portions in the mixture according to any one of the second aspect of the present application, or a part of the bispecific antibody or antigen binding portion thereof (such as a light chain and/or a heavy chain), or encoding the HER2 variant protein according to any one of the third aspect of the present application.

A fifth aspect of the present application relates to a recombinant vector, comprising the nucleic acid molecule according to any one of the fourth aspect of the present application.

A sixth aspect of the present application relates to a recombinant cell, comprising the recombinant vector according to any one of the fifth aspect or the nucleic acid molecule according to any one of the fourth aspect of the present application.

A seventh aspect of the present application relates to a method for preparing a bispecific antibody or antigen binding portion thereof based on two monoclonal antibodies or antigen binding portions thereof against different antigen epitopes, comprising the following step of:

obtaining a sequence of a common light chain capable of assembling with a heavy chain of the two monoclonal antibodies respectively based on light chain sequences of the two monoclonal antibodies, wherein said common light chain refers to two light chains having the same sequence, preferably, the common light chain is a light chain of one of the two monoclonal antibodies or a mutant of the light chain of one of the two monoclonal antibodies.

In one embodiment, the method further comprises the following steps of:

constructing expression vectors comprising the common light chain sequence and the heavy chain sequence of the two monoclonal antibodies, respectively, to obtain two recombinant expression vectors; preferably, mutating the heavy chain sequences, especially the Fc fragment, to facilitate aggregation of the Fc fragments of the two monoclonal antibodies having different heavy chains; and introducing the two recombinant expression vectors into the same host cell, and inducing expression to obtain the bispecific antibody or the antigen binding portion thereof.

In one embodiment, a variable region of the common light chain is obtained with the steps of: firstly determining interface amino acids in the light chain variable region of the two monoclonal antibodies contacting with their respective antigens or antigen epitopes, then designating the light chain variable region of one of the two monoclonal antibodies as a candidate common light chain variable region, comparing the interface amino acids in said candidate common light chain variable region with those in the light chain variable region of the other one of the two monoclonal antibodies when contacting with the antigen or antigen epitopes directed to by said one of the two monoclonal antibodies, to identify differential interface amino acids, and selecting a light chain variable region comprising fewer number of the differential interface amino acids as the common light chain variable region; preferably, further mutating the common light chain variable region to obtain a common light chain variable region having a better affinity to the corresponding antigen or antigen epitope. In one embodiment, a method of obtaining a constant region of the common light chain comprises the steps of: designating the light chain constant region of the monoclonal antibody providing a variable region of the common light chain as a common light chain constant region, or further mutating the light chain constant region to obtain a constant region of the common light chain.

In one embodiment, the mutation refers to modifications of the interface amino acids.

In one embodiment, better affinity with the antigen or antigen epitope means that the affinity between the common light chain and the two antigens or antigen epitopes directed to by the bispecific antibody or antigen binding portion thereof are balanced so that the bispecific antibody or antigen binding portion thereof has better biological activity and physicochemical properties (such as stability).

An eighth aspect of the present application relates to a method for preparing a mixture comprising at least two monoclonal antibodies or antigen binding portions thereof, comprising the following steps of:

obtaining a common light chain sequence capable of respectively assembling with heavy chains of two monoclonal antibodies respectively based on light chain sequences of the two monoclonal antibodies, wherein the common light chain refers to that the two light chains have the same sequence, preferably, the common light chain is a light chain of one of said two monoclonal antibodies or a mutant of a light chain of one of said two monoclonal antibodies.

In one embodiment, the method further comprises the following steps of:

constructing expression vectors comprising the common light chain sequence and the heavy chain sequence of the two monoclonal antibodies, respectively, to obtain two recombinant expression vectors; preferably, mutating the heavy chain sequences, especially the Fc fragment, to facilitate aggregation of the Fc fragments of the monoclonal antibodies having the same heavy chains; and introducing the two recombinant expression vectors into one host cell, and inducing expression to obtain a mixture of the antibodies or antigen binding portions thereof.

In one embodiment, a method of obtaining a variable region of the common light chain is obtained with the steps of: firstly determining interface amino acids in the light chain variable region of the two monoclonal antibodies contacting with their respective antigens or antigen epitopes, then designating the light chain variable region of one of the two monoclonal antibodies as a candidate common light chain variable region, comparing the interface amino acids in said candidate common light chain variable region with those in the light chain variable region of the other one of the two monoclonal antibodies when contacting with the antigen or antigen epitopes directed to by said one of the two monoclonal antibodies, to identify differential interface amino acids, and selecting a light chain variable region comprising fewer number of the differential interface amino acids as the common light chain variable region; preferably, further mutating the common light chain variable region to obtain a common light chain variable region having a better affinity to the corresponding antigen or antigen epitope. In one embodiment, a method of obtaining a constant region of the common light chain comprises the steps of: designating a light chain constant region of the monoclonal antibody providing a variable region of the common light chain as a common light chain constant region, or further mutating the light chain constant region to obtain a constant region of the common light chain.

In one embodiment, the mutation refers to a mutation of the interface amino acids.

In one embodiment, better affinity with the antigen or antigen epitope means that the affinity between the common light chain and two antigens or antigen epitopes directed to by the two monoclonal antibodies in the mixture are balanced so that the mixture has better biological activity and physicochemical properties (such as stability).

The present application also relates to a method for determining whether or not an antibody or antigen binding portion thereof is a bispecific antibody or antigen binding portion thereof and/or a method for quantifying the same, comprising the following steps of (see the diagram in FIG. 25):

1) preparing a first specific antigen and a second specific antigen respectively, wherein said first specific antigen is capable of binding to a first antigen binding portion but not to a second antigen binding portion in a bispecific antibody or an antigen binding portion thereof, and said second specific antigen is capable of binding to said second antigen binding portion but not to said first antigen binding portion;

2) coating an ELISA plate with the first specific antigen (or the second specific antigen), adding an antibody to be tested, after a period of reaction, adding the second specific antigen comprising a label (or the first specific antigen comprising a label), after a period of reaction, adding a detection molecule capable of binding to the label, after a period of reaction, and obtaining results according to the detection principle, thereby determining the reaction as positive or negative, wherein the detection molecule comprises a detectable label; and 3) when the reaction is positive and the result is concentration dependent, the antibody or antigen binding portion thereof is determined to be a bispecific antibody or antigen binding portion thereof; optionally, further quantifying the bispecific antibody or antigen binding portion thereof according to the obtained positive result.

In the present application, the first antigen binding portion and the second antigen binding portion respectively refers to two portions of a bispecific antibody or antigen binding portion thereof assembling with different antigens or antigen epitopes; in an embodiment, the first antigen binding portion and the second antigen binding portion are obtained respectively via modification on the basis of the two original antibodies, and the antigens or antigen epitopes directed to by the first antigen binding portion and the second antigen binding portion are the same as those directed to by the two original antibodies, respectively.

In one embodiment, the first antigen and the second antigen are HERm1 and HERm2.

In one embodiment, the labeled specific antigen is a specific antigen labeled with biotin.

In one embodiment, the detection molecule is a substrate molecule used for detection, such as HRP-labeled streptavidin.

The present application also relates to a method for determining whether or not a mixture of antibodies or antigen binding portions thereof comprises a homodimer protein, the mixture comprises two antibodies (a first antibody and a second antibody) or antigen binding portions thereof, and the method comprises the following steps of (see the diagram in FIG. 26):

1) preparing a first specific antigen and a second specific antigen respectively, wherein said first specific antigen is capable of binding to the first antibody but not to the second antibody, and said second specific antigen is capable of binding to the second antibody but not to the first antibody;

2) coating an ELISA plate with the first specific antigen (or the second specific antigen), adding the mixture to be tested, after a period of reaction, adding the first specific antigen comprising a label (or the second specific antigen comprising a label), after a period of reaction, adding a detection molecule capable of binding to the label, after a period of reaction, and obtaining results according to the detection principle, thereby determining the reaction as positive or negative, wherein the detection molecule comprises a detectable label;

3) separately, coating an ELISA plate with the first specific antigen (or the second specific antigen), adding the mixture to be tested, after a period of reaction, adding the second specific antigen comprising a label (or the first specific antigen comprising a label), after a period of reaction, adding a detection molecule capable of binding to the label, after a period of reaction, and obtaining results according to the detection principle, thereby determining the reaction as positive or negative, wherein the detection molecule comprises a detectable label;

4) when the reaction in the step 2) is positive and is concentration dependent and the reaction in the step 3) is negative, the mixture is determined to comprise a homodimer protein and does not comprise any heterodimer protein; when the reaction in the step 2) is positive and the reaction in step 3) is positive, the mixture is determined to comprise both homodimer protein and heterodimer protein.

In one embodiment, the first specific antigen and the second specific antigen are HERm1 and Herm2.

In one embodiment, the labeled specific antigen is an antigen labeled with biotin.

In one embodiment, the detection molecule is a substrate molecule used for detection, such as HRP-labeled streptavidin.

The present application also relates to a composition (such as a pharmaceutical composition), comprising the bispecific antibody or antigen binding portion thereof according to any one of the first aspect of the present application, and optionally pharmaceutically acceptable carrier or excipient.

The present application also relates to a composition (such as pharmaceutical composition, comprising a mixture according to any one of the second aspect of the present application, and an optional pharmaceutically acceptable carrier or excipient.

The present application also relates to a kit, comprising the bispecific antibody or antigen binding portion thereof according to any one of the first aspect of the present application, and optionally a buffer and/or an instruction.

In one embodiment, the kit is used for diagnosing HER2 positive tumor (such as breast cancer and gastric cancer).

The present application also relates to a kit, comprising a mixture according to any one of the second aspect of the present application, and optionally a buffer and/or an instruction.

In one embodiment, the kit is used for diagnosing HER2 positive tumor (such as breast cancer and gastric cancer).

The present application also relates to use of the bispecific antibody or antigen binding portion thereof according to any one of the first aspect of the present application in the manufacture of a medicament for preventing and/or treating HER2 positive tumor (such as breast cancer and gastric cancer).

The present application also relates to use of a mixture according to any one of the second aspect of the present application in the manufacture of a medicament for preventing and/or treating HER2 positive tumor (such as breast cancer and gastric cancer).

The present invention relates to use of the bispecific antibody or antigen binding portion thereof according to any one of the first aspect of the present application in the preparation of a reagent or a kit for diagnosing HER2 positive tumor (such as breast cancer and gastric cancer).

The present application also relates to use of the mixture according to any one of the second aspect of the present application in the preparation of a reagent or a kit for diagnosing HER2 positive tumor (such as breast cancer and gastric cancer).

The present application also relates to use of the variant protein of HER2 protein extracellular domain according to any one of the third aspect of the present application in the detection of the bispecific antibody or antigen binding portion thereof according to any one of the first aspect or in the detection of the mixture according to any one of the second aspect of the present application.

The present application also relates to a method for preventing and/or treating HER2 positive tumor (such as breast cancer and gastric cancer), comprising the step of administrating to a subject in need thereof a prevention or treatment effective amount of a bispecific antibody or antigen binding portion thereof according to any one of the first aspect of the present application.

The present application also relates to a method for preventing and/or treating HER2 positive tumor (such as breast cancer and gastric cancer), comprising a step of administrating to a subject in need thereof a prevention or treatment effective amount of a mixture according to any one of the second aspect of the present application.

The present application also relates to a method for diagnosing HER2 positive tumor (such as breast cancer and gastric cancer), comprising a step of using the bispecific antibody or antigen binding portion thereof according to any one of the first aspect of the present application.

The present application also relates to a method for diagnosing HER2 positive tumor (such as breast cancer and gastric cancer), comprising a step of using a mixture according to any one of the second aspect of the present application.

The present application also relates to a method for detecting the bispecific antibody or antigen binding portion thereof according to any one of the first aspect of the present application or detecting the mixture according to any one of the second aspect of the present application, comprising a step of using the variant protein of the HER2 protein extracellular domain according to any one of the third aspect of the present application.

The present application also relates to the bispecific antibody or antigen binding portion thereof according to any one of the first aspect of the present application for preventing and/or treating HER2 positive tumor (such as breast cancer and gastric cancer).

The present application also relates to the mixture according to any one of the second aspect of the present application for preventing and/or treating HER2 positive tumor (such as breast cancer and gastric cancer).

Inventions of the present application will be further described below.

In the present application, the term "antibody" refers to an immunoglobulin molecule consisting of two pairs of identical polypeptide chains (each pair has one (L) chain and one "heavy" (H) chain). A light chain of an antibody can be a κ light chain or a λ light chain. A heavy chain can be a μ, δ, γ, α or ε heavy chain, and the antibody isotype is correspondingly defined as IgM, IgD, IgG, IgA and IgE. Within the light chains and the heavy chains, variable regions and constant regions are connected through "J" regions which consist of about 12 or more amino acids, the heavy chains also comprise "D" regions which consist of about 3 or more amino acids. Each heavy chain consists of a heavy chain variable region (VH) and a heavy chain constant region (CH). The heavy chain constant region consists of 3 domains (CH1, CH2 and CH3). Each light chain consists of a light chain variable region (VL) and a light chain constant region (CL). The light chain constant region consists of one domain CL. The constant regions of the antibody can mediate binding of an immunoglobulin with a host cell or a factor, including binding of various cells (such as effector cells) of the immune system with a first component (C1q) of a classical complement system. VH and VL regions can also be subdivided into highly variable regions (named complementary determining regions (CDR)), and in between the CDRs, conservative regions known as framework regions (FR) are distributed. Each VH and each VL consists of 3 CDRs and 4 FRs arranged from amino terminals to carboxyl terminals in a sequence of FR1, CDR1, FR2, CDR2, FR3, CDR3 and FR4. Variable regions (VH and VL) of each heavy chain/light chain pair respectively form antibody binding portions. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196:901-917, or Chothia et al (1989) Nature 342:878-883. The term "antibody" is not limited by any specific method for producing an antibody. For example, it comprises, particularly, a recombinant antibody, a monoclonal antibody and a polyclonal antibody. The antibodies can be antibodies of various isotypes, for example, IgG (such as IgG1, IgG2, IgG3 or IgG4 subtype), IgA1, IgA2, IgD, IgE or IgM antibody.

In the present application, the term "antigen binding portion" of the antibody refers to one or more portions of a full-length antibody, the antigen binding portion maintains the ability of binding to an antigen (such as HER2) that is the same as that bound by the antibody, and competes with the full-length antibody for the specific binding to an antigen. General reference is made to Fundamental Immunology, Ch. 7 (Paul, W., ed., edition II, Raven Press, N.Y. (1989), which is incorporated herein by reference in its entirety and for all purposes. The antigen binding portion can be produced using a recombinant DNA technology or through enzymatic or chemical breakage of a full-length antibody. In some cases, the antigen binding portion comprises a polypeptide such as a Fab, a Fab', a F(ab')2, a Fd, a Fv, a dAb, a complementary determining region (CDR) fragment, a single-chain antibody (such as a scFv), a chimeric antibody, and a diabody, and it comprises at least the part of the antibody sufficiently endowing the polypeptide with the specific antigen binding ability. The antigen binding portion (such as the above antibody fragment) of the antibody may be obtained from a given antibody (such as monoclonal antibody 2E12) using a conventional technology (such as recombinant DNA technology or enzymatic or chemical breakage process) known to those skilled in the art, and are screened for its specificity in a process that is the same for screening full-length antibodies.

In the present application, the term "Fd fragment" refers to an antibody fragment consisting of $V_H$ and $C_H1$ domains; the term "Fv fragment" refers to an antibody fragment consisting of $V_L$ and $V_H$ domains of a single arm of an antibody; the term "dAb fragment" refers to an antibody fragment consisting of a $V_H$ domain (Ward et al, Nature 341:544-546 (1989)); the term "Fab fragment" refers to an antibody consisting of $V_L$, $V_H$, $C_L$ and $C_H1$ domains; and the term "F(ab')2 fragment" refers to an antibody fragment comprising two Fab fragments connected through a disulfide bridge in a hinge region.

In the present application, the term "antibody Fc fragment" is a term known to those skilled in the art and is defined based on proteolysis of an antibody by papain, and refers to a human immunoglobulin chain constant region, especially a carboxyl terminal of an immunoglobulin heavy chain constant region or a part thereof. For example, an immunoglobulin Fc region may comprise combinations of two or more domains selected from heavy chain CH2, CH3 and CH4 with an immunoglobulin hinge region. Based on amino acid sequences of the heavy chain constant region, immunoglobulins may be divided into different types, mainly the following five types: IgA, IgD, IgE, IgG and IgM, some of which can be further divided into subtypes (isotypes), for example, IgG-1, IgG-2, IgG-3, IgG-4, IgA-1 and IgA-2. Selecting specific immunoglobulin Fc regions from specific types and subtypes of the immunoglobulin is within the knowledge of those skilled in the art.

In one embodiment, the antibody Fc fragment used in the present application comprises at least one immunoglobulin hinge region, one CH2 domain and one CH3 domain, for example, a human IgG1 Fc.

In the present application, the term "bispecific antibody" refers to an antibody that can respectively bind with two antigens or antigen epitopes, comprising a light chain and a heavy chain of an antibody capable of specifically binding to a first antigen or antigen epitope, and a light chain and a heavy chain of an antibody capable of specifically binding to a second antigen or antigen epitope. In one embodiment, in the bispecific antibody, the antibody light chain capable of specifically binding to a first antigen or antigen epitope and the antibody light chain capable of specifically binding to a second antigen or antigen epitope have the same sequences. In one embodiment, in the bispecific antibody, the antibody heavy chain capable of specifically binding to a first antigen or antigen epitope and the antibody heavy chain capable of specifically binding to a second antigen or antigen epitope have different sequences.

In the present application, the term "epitope" or "antigen epitope" refers to a portion in an antigen specifically bound by an immunoglobulin or an antibody. "Epitope" is also known as "antigenic determinant". The "epitope" or "antigenic determinant" often consists of chemical reactive surface groups of a molecule, such as amino acid or carbohydrate or glycosyl side chains, and often has specific three-dimensional structure features and specific charge features. For example, the epitope, which can be "linear" or "conformational", often comprises at least 3, 4, 5, 6, 7, 8, 9, 10, 11, 12, 13, 14 or 15 continuous or non-continuous amino acids in a unique spatial conformation. See the reference, for example, Epitope Mapping Protocols in Methods in Molecular Biology, volume 66, G. E. Morris, Ed. (1996). In a linear epitope, all the interaction sites between a protein and a molecule that it interacts with (such as an antibody) are arranged linearly along the primary amino acid sequence of the protein. In a conformational epitope, interaction sites are arranged across the protein at discrete sites separate from each other.

In the present application, 20 conventional amino acids and abbreviations thereof comply with conventional rules. Reference may be made to, Immunology—A Synthesis (Edition II, E. S. Golub and D. R. Gren, Eds., Sinauer Associates, Sunderland, Mass. (1991)), which is incorporated herein by reference.

In the present application, light chain sequences (especially variable region sequences) of two monoclonal antibodies (namely original antibodies) against different antigens or antigen epitopes are analyzed and verified to obtain a common light chain capable of assembling with the heavy chains of the two monoclonal antibodies. After assembling with the heavy chains, the common light chain still can specifically bind to the antigens or antigen epitopes directed to by the original monoclonal antibodies.

In the present application, the common light chain can be used for expressing the bispecific antibody, and can also be used for expressing a mixture comprising two antibodies; when the bispecific antibody is expressed, the antibody comprises a light chain and a heavy chain which are capable of binding to a first antigen, and a light chain and a heavy chain which are capable of binding to a second antigen, wherein the sequences of the two light chain are completely the same, namely, is a common light chain; and when the antibody mixture is expressed, each antibody respectively comprises two light chains and heavy chains, wherein sequences of the light chains are completely the same, namely, is the common light chain.

In the present application, light chain constant regions of the two original antibodies can be of κ type or λ type; the κ-type light chain constant region comprises various allotypes, such as Km1, Km2 and Km3; the λ-type light chain constant region comprises various allotypes, such as CL1, CL2, CL3, CL6 and CL7.

It is known in the art that the variable region is crucial for specific binding between the antigen and the antibody, thus, during the process of modifying or obtaining an antibody, the selection and modification of the variable region sequences are critical. Hence, in the present application, in order to obtain the bispecific antibody or the antibody mixture having the common light chain, the variable regions of the common light chain need to be obtained firstly. After selecting the light chain variable region of one original monoclonal antibody or a mutant thereof as the variable region of the common light chain according to the method discussed above, the constant region of the common light chain is determined. Normally, the common light chain constant region is determined to be the light chain constant region of the monoclonal antibody from which the common light chain variable region is derived. In some cases, the light chain constant region of the other monoclonal antibody may be determined to be the common light chain constant region. When necessary, the original light chain constant region can be modified (e.g., by addition, deletion or mutation of amino acid, etc.) based on knowledge known in the art to obtain a more suitable constant region of the common light chain, for example, after modification, the common light chain constant region has a better ADCC, CDC, endocytosis, stability, immunogenicity or half-life etc.

In the present application, the heavy chain type of the two original antibodies can be the same or different, preferably, the heavy chains are of the same type. In one embodiment, when preparing the bispecific antibody and the antibody mixture, the sequences of the variable region and the CH1 domain of the heavy chain are unchanged comparing to that of the original antibodies.

In the present application, two arms of the bispecific antibody or the antibodies of the mixture containing two antibodies are both derived from two original monoclonal antibodies. When preparing the bispecific antibody or the antibody mixture, only sequences of the light chain variable region would be changed to obtain the common light chain, while sequences of the heavy chain variable region do not need to be changed. In other words, in the bispecific antibody or the antibody mixture prepared, sequences of the antibody heavy chain variable regions may be the same as that of the original antibody, but sequences of at least one light chain variable region shall be different from that of the original antibody.

In the present application, the two original monoclonal antibodies can be selected according to different demands or objectives, for example, the selected two monoclonal antibodies can be against different antigen epitopes of the same antigen; alternatively, one of selected antibodies may bind to a related antigen on the surface of a tumor cell while the other antibody may trigger an immunologic effector cell so as to further kill a cell.

In the present application, when preparing the bispecific antibody, the heavy chain (such as an Fc fragment) can be modified based on technologies known in the art to facilitate formation of the heterodimer protein during antibody expression.

In the present application, when preparing the antibody mixture, the heavy chain (such as an Fc fragment), can be modified based on technologies known in the art so as to facilitate formation of the homodimer protein during antibody expression.

In the present application, technologies for modifying an Fc fragment of the antibody heavy chain to facilitate formation of the homodimer protein or the heterodimer protein are known in the art, for example, reference may be made to, Ridgway, Presta et al. 1996, Carter 2001, Patent CN 102558355A and Patent CN 103388013A.

In the present application, technologies of fusing polypeptides recognizing different antigen epitopes include but is not limited to, for example, a heterodimer Fc fusing technology as shown in the examples, it can also be an "Fab" technology, see FIG. 1.

In the present application, the heterodimer Fc fusing technology used in the present application may be based on a "knob"-"hole" model, and it may also be based on a "charge repulsion model", but is not limited to these two models.

In the present application, the platform capable of producing and preparing antibody mixtures in a single recombinant cell as used in the present application may be based on the "charge repulsion" model, but is not limited to this model.

In some embodiments of the present application, when preparing the bispecific antibody or the antibody mixture, the nucleic acid molecule encodes a light chain and/or heavy chain of an antibody against a first antigen, or encodes a light chain and/or heavy chain of an antibody against a second antigen. In some embodiments of the present application, the light chain is the common light chain; in some embodiments of the present application, the Fc fragment of the heavy chain is modified.

In some embodiments of the present application, the vector can be a cloning vector or an expression vector. The cloning vector is used for cloning a related fragment of an antibody; the expression vector is used for expressing a bispecific antibody or an antibody mixture. A vector suitable for antibody expression can be selected according to common knowledge in the art. In some embodiments of the present application, the expression vector is pcDNA4m, which is obtained by modifying the vector pcDNA4/myc-HisA.

In some embodiments of the present application, the expression vector comprises a nucleic acid molecule encoding the light chain and/or heavy chain of the antibody against the first antigen, or a nucleic acid molecule encoding the light chain and/or heavy chain of the antibody against the second antigen.

In some embodiments of the present application, the host cell is a host cell suitable for the expression of the antibody, for example, a prokaryotic cell (such as *E. Coli*) or a eukaryotic cell; the eukaryotic cell, for example, is a yeast cell, a plant cell or a mammal cell, and the mammal cell, for example, is a CHO cell, HEK293 cell or a myeloma cell, etc.

In some embodiments of the present application, the host cell simultaneously comprises an expression vector which is capable of expressing the light chain and/or heavy chain of an antibody against the first antigen and an expression vector which is capable of expressing the light chain and/or heavy chain of an antibody against the second antigen; in some embodiments of the present invention, the light chain is the common light chain; in some embodiments of the present application, the Fc fragment of the heavy chain is modified. When the host cell is used to express a bispecific antibody, through a modification of the Fc fragment, the light chains and heavy chains of antibodies against different antigens are more easily to assemble to form the bispecific antibody; when the host cell is used to express an antibody mixture, through a modification of the Fc fragment, light chains and heavy chains of antibodies against the same antigen are more easily to assemble to form the antibody mixture.

The bispecific antibody or the antibody mixture can be purified from the host cell using standard experiment approaches. Purification methods include but are not limited to a chromatographic technique such as volume exclusion, ion exchange, affinity chromatography and ultrafiltration. In some embodiments of the present application, a bispecific antibody and an antibody mixture are purified with ProteinA affinity chromatography.

In the present application, the bispecific antibody or antigen binding portion thereof or the mixture thereof can also be co-administered with a chemotherapeutic drug and/or other antibodies, thus a composition of the present application may also comprise a chemotherapeutic drug and/or other antibodies.

In the present application, the chemotherapeutic drug includes but is not limited to Adriamycin, cyclophosph- amide and taxane [Taxol and Taxotere], Xeloda, Gemzar, Navelbine, Tamoxifen, aromatase inhibitors (Arimidex, Felon and Arnoux), 5-FU & folinic acid, camptosar, Oxali-platin, cis-plantinum, Paraplatin, Estramustin, Novantrone, Metacortandracin, Oncovin etc., or a combination thereof.

In the present application, by mutating a HER2 protein, a HER2 protein mutant capable of only specifically binding to one of Pertuzumab and HERCEPTIN® (trastuzumab) is obtained. In some embodiments of the present application, the HER2 protein mutant is used to identify the bispecific antibody and the antibody mixture.

In the present application, double-antigen sandwich ELISA (also known as bridge ELISA) is used in combination with the HER2 protein mutant to determine whether or not the antibody is a bispecific antibody, or whether or not the antibody mixture comprises a homodimer protein, further, to quantify the bispecific antibody or homodimer proteins in the antibody mixture.

In the present application, the double-antigen sandwich ELISA method is known in the art, and its principle is that an antigen bound to a solid support and an enzyme labeled antigen are used to respectively bind to the two antigen binding sites of a candidate antibody molecule in a sample, forming a solid phase antigen-antibody-enzyme labeled antigen immune complex. The detection steps of this method, for example, comprise: (1) coating a solid support with a specific antigen, incubating for a period of time to form a solid support antigen, washing and removing unbound antigen and impurities; (2) adding a sample and incubating for the antibodies in the sample and the antigen on the solid support to interact sufficiently so as to form a solid support antigen-antibody complex, and washing and removing other unbound substances; (3) adding an enzyme labeled antigen, incubating to form a solid support antigen-candidate antibody-enzyme labeled antigen sandwich complex, and washing and removing any unbound enzyme labeled antigen; (4) adding a substrate for color developing. Enzymes on the solid support will catalyze the substrate to produce a colored product, and the quantity of the antibodies in the sample may be measured with colorimetry.

In the present application, a HER2 positive tumor comprises a HER2 protein over-expressed tumor (such as breast cancer, a gastric cancer, esophagus cancer, ovarian cancer, endometrial cancer, bladder cancer, lung cancer, colon cancer and head and neck neoplasm), and also comprises a HER2 protein under-expressed tumor (such as HER2 under-expressed breast cancer and lung cancer).

In the present application, a common light chain capable of respectively assembling with heavy chains of two different antibodies can be obtained through the analysis of sequences of the light chains of the two antibodies, and a bispecific antibody and an antibody mixture having the common light chain are prepared accordingly. Experimental results demonstrated that the bispecific antibody and the antibody mixture prepared by the method has good binding activity, biological activity and stability, and has better biological activity than the original antibody.

The common light chain technology is simple and controllable, and effectively solves the problem of mismatching between heavy chains and light chains of bispecific antibodies, while the stability, activity and purity of the bispecific antibodies are not affected. For antibody mixtures, the common light chain technology allows antibodies to be expressed in the same host cell, which avoids the difficulties of mixed cell population culture and facilitate large-scale production.

DETAILED DESCRIPTION

Figure 1:
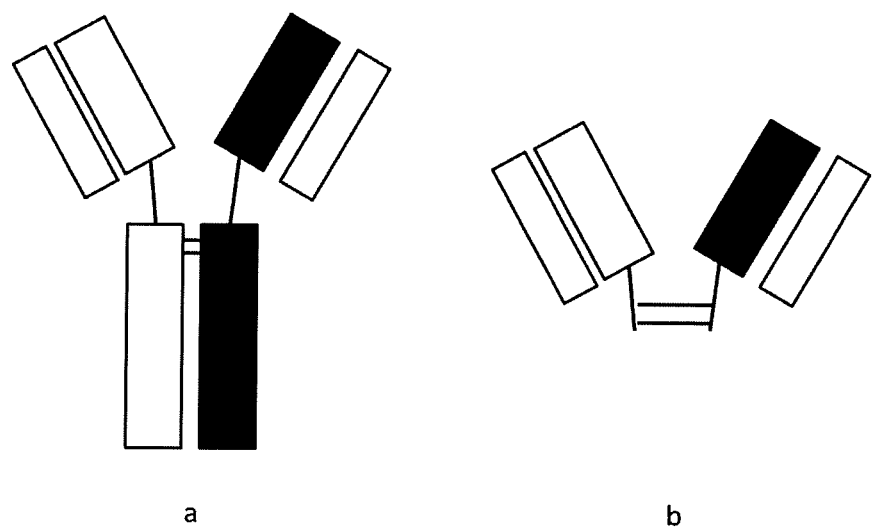
FIG. 1 is a schematic diagram of heterodimer protein fusion. Panel a illustrates a heterodimer Fc fusion technology, and Panel b illustrates a "Fab" technology.

The embodiments of the present application will be described in detail in light of the examples, but it will be understood by those skilled in the art that the examples below are only for illustrating the present application, rather than for limiting the scope of the present application. Where specific conditions are not indicated, the experiments are usually carried out in accordance with conventional conditions or conditions recommended by the manufacturer. Where sources of the reagents or devices used are not indicated, conventional products available on the market were used.

Example 1 Obtainment of Common Light Chain

1. Obtainment of Sequences and Structures

Complex crystal structures of Trastuzumab and Pertuzumab are obtained from a protein data bank respectively, the PDB number of Trastuzumab is 1N8Z, and the PDB number of Pertuzumab is 1S78. Two screening strategies can be used to identify amino acid contacts between CH3-CH3: (i) distance of amino acid interaction and (ii) solvent accessibility region analysis. Here, the analysis was performed according to the distance of amino acid interaction.

2. Obtainment of Monoclonal Antibody Light Chain and Antigen HER2 Interface Amino Acid In accordance with the principles of amino acid contact, the interface amino acids refer to such amino acids: the distance between a heavy atom of a side chain of the amino acid and a heavy atom of any amino acid from another peptide chain is less than a threshold value. Here, the threshold value was determined to be 4.5 Å. 5.5 Å can also be used in some cases (Bahar and Jernigan 1997). Table 1 is a list of amino acids mediating contact between a Trastuzumab light chain and the antigen HER2. 12 interface amino acids of Trastuzumab are shown in the Table 1, which are selected according to the principles of amino acid contact.

TABLE 1

Trastuzumab light chain-antigen HER2 interface amino acid list

| Trastuzumab Light Chain | Antigen HER2 |
|---|---|
| ASP28A(CL1) | GLU598C |
| ASN30A(CL1) | PRO571C, ASP596C, GLU598C, ALA600C, CYS601C, GLN602C |
| THR31A(CL1) | CYS601C, GLN602C, PRO603C |
| ALA32A(CL1) | PRO571C |
| TYR49A | PRO603C |
| SER50A(CL2) | LYS593C, PRO603C |
| PHE53A(CL2) | PRO603C, CYS604C, PRO605C |
| ARG66A | ASP596C, GLU598C |
| HIS91A(CL3) | ASP570C, PRO571C, PRO572C |
| TYR92A(CL3) | LYS569C, PRO571C, PRO572C, GLU598C, ALA600C |
| THR93A(CL3) | ASP560C, PRO572C |
| THR94A(CL3) | ASP560C, PRO572C |

Table 2 is a list of amino acids mediating contact between a Pertuzumab light chain and an antigen HER2. 8 interface amino acids of Pertuzumab are shown in the Table 2, which are selected according to the principles of amino acid contact.

TABLE 2

Pertuzumab light chain and antigen HER2 interface amino acid list

| Pertuzumab Light Chain | Antigen HER2 |
|---|---|
| ILE31C(CL1) | SER313A |
| LEU46C | HIS296A |
| TYR49C | HIS296A, CYS312A, SER313A, LYS314A, PRO315A |
| SER50C(CL2) | SER313A |
| TYR53C(CL2) | SER313A, LYS314A, PRO315A |
| TYR55C(CL2) | LEU295A, HIS296A |
| THR56C(CL2) | LEU295A, HIS296A |
| TYR94C(CL3) | THR254A, ASP255A, THR256A, PHE257A |

3. Identification of Pertuzumab and Trastuzumab Light Chain Hyperviable Regions (CDRL1, CDRL2, CDRL3)

Figure 2:
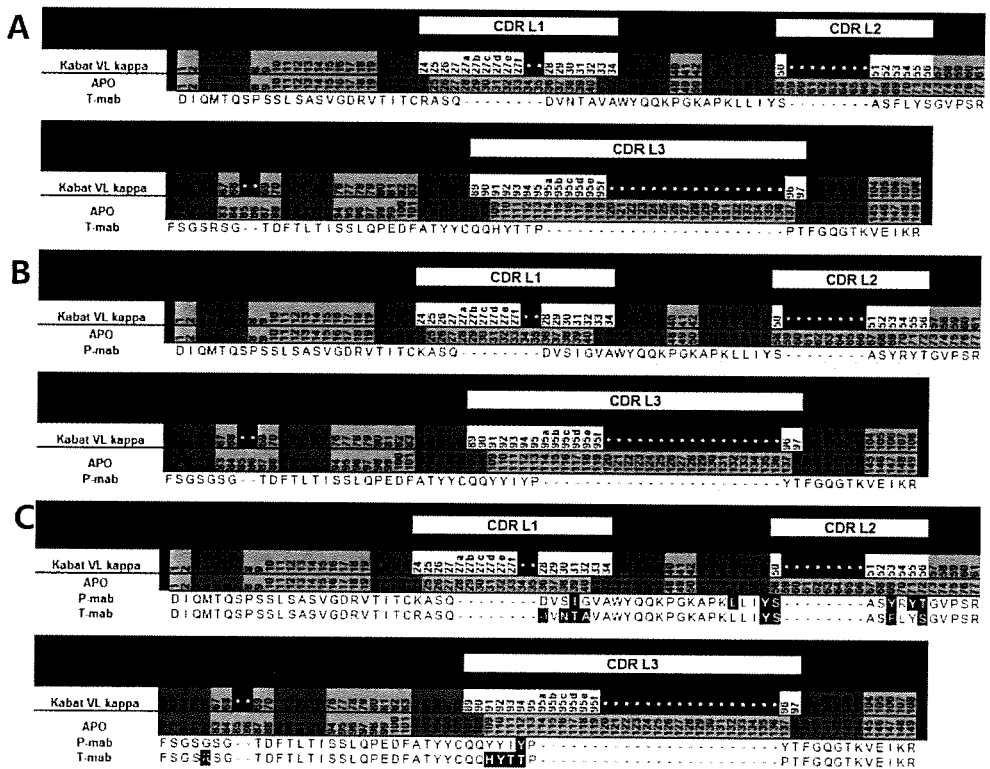
FIG. 2 illustrates recognition of light chain hypervariable regions of Pertuzumab and Trastuzumab, wherein A demonstrates the recognition result of a light chain hypervariable region of Pertuzumab, B demonstrates the recognition result of a light chain hypervariable region of Trastuzumab, and C demonstrates a comparison result of Pertuzumab and Trastuzumab light chains and shows a comprehensive analysis result of the antigen interface amino acid. T-mab indicates amino acids 1-107 of SEQ ID NO: 1, and P-mab indicates amino acids 1-107 of SEQ ID NO: 5.

Pertuzumab and Trastuzumab light chains are identified using hypervariable region recognition system-kabat numbering. The identification result for a Pertuzumab light chain hypervariable region is shown in FIG. 2-A, and the identification result of a Trastuzumab light chain hypervariable region is shown in FIG. 2-B.

4. Comparison of Pertuzumab and Trastuzumab Light Chain Sequences and Comprehensive Analysis of Light Chain and Antigen Interface Amino Acids A comparison result of the sequences of a Pertuzumab light chain and a Trastuzumab light chain and the results of a comprehensive analysis of antigen interface amino acids are shown in FIG. 2-C, the amino acids of Pertuzumab (P-mab) and Trastuzumab (T-mab) light chains contacting with the antigen are shown in background black color. If the Trastuzumab light chain is designated as the common light chain, then differential amino acids obtained by comparing the interface amino acids in the common light chain contacting with the antigen with those in the light chain of Pertuzumab (P-mab) are shown in Table 3.

TABLE 3

Differential amino acids contacting with antigen from the light chain of Pertuzumab (P-mab) and Trastuzumab (T-mab)

| Kabat number | P-mab | T-mab |
|---|---|---|
| Kabat31 | I | T |
| Kabat53 | Y | F |
| Kabat56 | T | S |
| Kabat94 | Y | T |

If the Pertuzumab light chain is designated as the common light chain, then differential amino acids obtained by comparing the interface amino acids in the common light chain contacting with the antigen with those in the light chain of Trastuzumab (T-mab) are shown in Table 4.

TABLE 4

Differential amino acids contacting with the antigen from the light chain of Pertuzumab (P-mab) and Trastuzumab (T-mab)

| Kabat number | P-mab | T-mab |
|---|---|---|
| Kabat30 | S | N |
| Kabat31 | I | T |
| Kabat32 | G | A |
| Kabat53 | Y | F |
| Kabat56 | T | S |
| Kabat66 | G | R |
| Kabat91 | Y | H |
| Kabat93 | I | T |
| Kabat94 | Y | T |

By analyzing the differential amino acids contacting with the antigen from the light chain of Pertuzumab (P-mab) and Trastuzumab (T-mab), the light chain of Trastuzumab (T-mab) was selected as a framework and the mutation T31I or/and T94Y were introduced to obtain a sequence of a common light chain of a Pertuzumab and Trastuzumab bispecific antibody: CLC1-CLC4; a light chain of Pertuzumab (P-mab) was selected as a framework and the mutation of T31I or/and T94Y were introduced to obtain a sequence of a common light chain of a Pertuzumab and Trastuzumab bispecific antibody: CLC5-CLC6. Amino acid sequences of the obtained common light chain are as follows:

CLC1
(SEQ ID NO: 1)
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

CLC2
(SEQ ID NO: 2)
DIQMTQSPSSLSASVGDRVTITCRASQDVNIAVAWYQQKPGKAPKLLIY

SASFLYSGVPSRFSGSRSGTDFTLTISSLQPEDFATYYCQQHYTTPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

-continued

CLC3
(SEQ ID NO: 3)
DIQMTQSPSSLSASVGDRVTITCRASQDVNTAVAWYQQKPGKAPKLLIY

SASFLYSGVPSRFSGSRSGTDFTLTISSLQPEDFATYYCQQHYTYPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

CLC4
(SEQ ID NO: 4)
DIQMTQSPSSLSASVGDRVTITCRASQDVNIAVAWYQQKPGKAPKLLIY

SASFLYSGVPSRFSGSRSGTDFTLTISSLQPEDFATYYCQQHYTYPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

CLC5
(SEQ ID NO: 5)
DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTFG

QGTKVEIKRTVAAPSVFIFPPSDEQLKSGTASVVCLLNNEYPREAKVQWK

VDNALQSGNSQESVTEQDSKDSTYSLSSTLTLSKADYEKHKVYACEVTHQ

GLSSPVTKSFNRGEC

CLC6
(SEQ ID NO: 6)
DIQMTQSPSSLSASVGDRVTITCKASQDVSIGVAWYQQKPGKAPKLLIY

SASYRYTGVPSRFSGSGSGTDFTLTISSLQPEDFATYYCQQYYITPYTFG

QGTKVEIKRTVAAPSVFIFPPSDEQLKSGTASVVCLLNNEYPREAKVQWK

VDNALQSGNSQESVTEQDSKDSTYSLSSTLTLSKADYEKHKVYACEVTHQ

GLSSPVTKSFNRGEC

Example 2 Preparation and Functional Verification of Antigen Protein HER2 Variant Protein 1. Design of HER2 Variant Protein Only Binding to Pertuzumab Robert F. Kelley and Mark P. O'Connell published kinetic parameters of the binding of Trastuzumab and its corresponding mutant and HER2 extracellular domain (ECD) in 1993. Wherein, H91A, R50A, W95A and Y100aA had great influence on the binding of Trastuzumab to HER2 extracellular domain. The team of Hyun-Soo Cho obtained crystals (PDB number: 1N8Z) of a complex formed between a Trastuzumab Fab fragment and HER2 extracellular domain (ECD) in 2003, and this result was published in Nature. By analyzing the structure of the complex formed by the Trastuzumab Fab fragment and the HER2 extracellular domain (ECD) (the sequence of which is shown in SEQ ID NO:18), interface contacting amino acids of the Trastuzumab Fab fragment and the HER2 extracellular domain (ECD) were obtained, as shown in Table 5.

H91L, R50H, W95H, Y100aH contacting amino acids were specifically analyzed. It was found that two combinations may significantly affect binding of these amino acids. Combination 1: ASP570, PRO571 and PRO572, and combination 2: GLU558 and PHE573.

TABLE 5

Interface contacting amino acids of Trastuzumab Fab fragment and HER2 extracellular domain (ECD)

| Number | Trastuzumab light chain | Antigen HER2 |
|---|---|---|
| 1 | ASP28L(CL1) | GLU598C |
| 2 | ASN30L(CL1) | PRO571C, ASP596C, GLU598C, ALA600C, CYS601C, GLN602C |
| 3 | THR31L(CL1) | CYS601C, GLN602C, PRO603C |
| 4 | ALA32L(CL1) | PRO571C |
| 5 | TYR49L | PRO603C |
| 6 | SER50L(CL2) | LYS593C, PRO603C |
| 7 | PHE53L(CL2) | PRO603C, CYS604C, PRO605C |
| 8 | ARG66L | ASP596C, GLU598C |
| 9 | HIS91L(CL3) | ASP570C, PRO571C, PRO572C |
| 10 | TYR92L(CL3) | LYS569C, PRO571C, PRO572C, GLU598C, ALA600C |
| 11 | THR93L(CL3) | ASP560C, PRO572C |
| 12 | THR94L(CL3) | ASP560C, PRO572C |
| 13 | TYR33H | GLU558C, PHE573C |
| 14 | ARG50H | GLU558C, ASP560C, PRO572C, PHE573C |
| 15 | TYR52H | GLU558C |
| 16 | TYR57H | TYR532C, PRO540C, PRO557C, GLU558C |
| 17 | THR58H | GLU558C |
| 18 | ARG59H | GLU558C, ASP560C, GLN561C |
| 19 | TRP99H | PRO572C, PHE573C |
| 20 | GLY101H | ILE591C |
| 21 | ASP102H | PRO579C, ILE591C |
| 22 | GLY103H | ASP570C, PRO579C, ILE591C, LYS593C |
| 23 | PHE104H | ILE591C, LYS593C |
| 24 | TYR105H | ASP570C, PRO571C, PRO572C, PHE573C, VAL575C, LYS593C |

It can be seen from the above result that:

combination 1: P571 and P572 interact with several critical amino acids of the Fab. It was believed that these two amino acids locate in a loop corner, and mutating them will influence the stability of its own structure.

combination 2: GLU588 forms an ion bond with and a Trastuzumab Fab heavy chain ARG 50, and forms Vander Waals' forces with multiple amino acids of the Fab heavy chain, destroying these interaction forces would block interactions between Trastuzumab Fab and HER2, and thus the mutation GLU558 to ALA558 was selected; Vander Waals' forces were formed between PHE573 and multiple amino acids of the Fab heavy chain, including critical amino acids ARG 508, TRP99 and TYP105, destroying these interaction forces would block interactions between the Fab and HER2, and thus the mutation PHE573 to ALA573 was selected.

Figure 3:
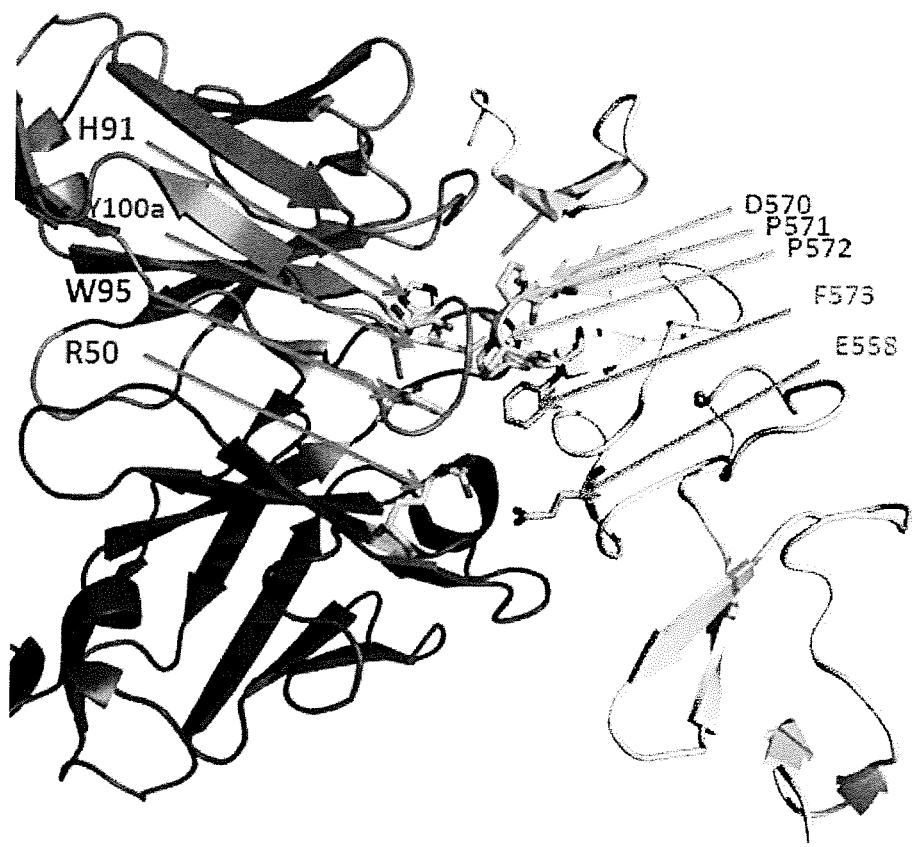
FIG. 3 is a structural diagram of a Trastuzumab Fab fragment and a Her2 extracellular domain (ECD).

The above analysis results are shown in FIG. 3.

2. Design of a HER2 Variant Protein Only Binding to Trastuzumab

Matthew C. Franklin published the structure of a complex formed between Pertuzumab Fab and an HER2 extracellular domain in Cancer Cell. This team also found which critical amino acids of HER2 can influence binding to Pertuzumab Fab using the alanine scanning method. The results show that amino acids, such as H296, S288 and L295 on the surface of the HER2 protein had significant effects, and in the present application, S288A/H296A double-mutation was selected to obtain the HER2 antigen only binding to Trastuzumab.

Wherein, a HER2 variant protein only recognized by Trastuzumab was named HER2m1, the HER2 variant proteins only recognized by Pertuzumab were named HER2m2 and HER2m3. The amino acid sequences of these HER2 variant proteins are as follows:

HER2m1:
(SEQ ID NO: 13)
TQVCTGTDMKLRLPASPETHLDMLRHLYQGCQVVQGNLELTYLPTNAS

LSFLQDIQEVQGYVLIAHNQVRQVPLQRLRIVRGTQLFEDNYALAVLDN

GDPLNNTTPVTGASPGGLRELQLRSLTEILKGGVLIQRNPQLCYQDTIL

WKDIFHKNNQLALTLIDTNRSRACHPCSPMCKGSRCWGESSEDCQSLTR

TVCAGGCARCKGPLPTDCCHEQCAAGCTGPKHSDCLACLHFNHSGICEL

HCPALVTYNTDTFESMPNPEGRYTFGASCVTACPYNYLSTDVGACTLVC

PLANQEVTAEDGTQRCEKCSKPCARVCYGLGMEHLREVRAVTSANIQEF

AGCKKIFGSLAFLPESFDGDPASNTAPLQPEQLQVFETLEEITGYLYIS

AWPDSLPDLSVFQNLQVIRGRILHNGAYSLTLQGLGISWLGLRSLRELG

SGLALIHHNTHLCFVHTVPWDQLFRNPHQALLHTANRPEDECVGEGLAC

HQLCARGHCWGPGPTQCVNCSQFLRGQECVEECRVLQGLPREYVNARHC

LPCHPECQPQNGSVTCFGPEADQCVACAHYKDPPFCVARCPSGVKPDLS

YMPIWKFPDEEGACQPCPINCTHSCVDLDDKGCPAEQRASPLT

HER2m2:
(SEQ ID NO: 14)
TQVCTGTDMKLRLPASPETHLDMLRHLYQGCQVVQGNLELTYLPTNAS

LSFLQDIQEVQGYVLIAHNQVRQVPLQRLRIVRGTQLFEDNYALAVLDN

GDPLNNTTPVTGASPGGLRELQLRSLTEILKGGVLIQRNPQLCYQDTIL

WKDIFHKNNQLALTLIDTNRSRACHPCSPMCKGSRCWGESSEDCQSLTR

TVCAGGCARCKGPLPTDCCHEQCAAGCTGPKHSDCLACLHFNHSGICEL

HCPALVTYNTDTFESMPNPEGRYTFGASCVTACPYNYLSTDVGSCTLVC

PLHNQEVTAEDGTQRCEKCSKPCARVCYGLGMEHLREVRAVTSANIQEF

AGCKKIEGSLAFLPESFDGDPASNTAPLQPEQLQVFETLEEITGYLYIS

AWPDSLPDLSVFQNLQVIRGRILHNGAYSLTLQGLGISWLGLRSLRELG

SGLALIHHNTHLCFVHTVPWDQLFRNPHQALLHTANRPEDECVGEGLAC

HQLCARGHCWGPGPTQCVNCSQFLRGQECVEECRVLQGLPREYVNARHC

LPCHPECQPQNGSVTCFGPAADQCVACAHYKDPAFCVARCPSGVKPDLS

YMPIWKFPDEEGACQPCPINCTHSCVDLDDKGCPAEQRASPLT

HER2m3:
(SEQ ID NO: 15)
TQVCTGTDMKLRLPASPETHLDMLRHLYQGCQVVQGNLELTYLPTNAS

LSFLQDIQEVQGYVLIAHNQVRQVPLQRLRIVRGTQLFEDNYALAVLDN

GDPLNNTTPVTGASPGGLRELQLRSLTEILKGGVLIQRNPQLCYQDTIL

WKDIFHKNNQLALTLIDTNRSRACHPCSPMCKGSRCWGESSEDCQSLTR

TVCAGGCARCKGPLPTDCCHEQCAAGCTGPKHSDCLACLHFNHSGICEL

HCPALVTYNTDTFESMPNPEGRYTFGASCVTACPYNYLSTDVGSCTLVC

PLHNQEVTAEDGTQRCEKCSKPCARVCYGLGMEHLREVRAVTSANIQEF

AGCKKIFGSLAFLPESFDGDPASNTAPLQPEQLQVFETLEEITGYLYIS

AWPDSLPDLSVFQNLQVIRGRILHNGAYSLTLQGLGISWLGLRSLRELG

SGLALIHHNTHLCFVHTVPWDQLFRNPHQALLHTANRPEDECVGEGLAC

HQLCARGHCWGPGPTQCVNCSQFLRGQECVEECRVLQGLPREYVNARHC

LPCHPECQPQNGSVTCFGPEADQCVACAHYKDAAFCVARCPSGVKPDLS

YMPIWKFPDEEGACQPCPINCTHSCVDLDDKGCPAEQRASPLT

3. Modification of Commercial Mammalian Cell Expression Vector pcDNA4/Myc-HisA

The commercial vector pcDNA4/myc-HisA (Invitrogen, V863-20) comprises two PvuII restriction enzyme recognition sites which are located at the positions of about 1411 bp and 3160 bp, respectively. Site-directed mutagenesis was carried out on the plasmid so that a residue C at the position 3160 bp was mutated into G, and the PvuII restriction enzyme recognition site at this position was removed while only one restriction enzyme recognition site at the position of about 1411 bp remained, and the new vector was named as pcDNA4m.

Primers are designed in accordance with a DNA sequence (AY623427) of a crystallizable fragment (Fc) of human immunoglobulin gamma1 (IgG1) from NCBI as follows:

F:
(SEQ ID NO: 29)
AAGCTTCCCTTACCCGGATCCGAAATCCTCTGACAAAACTCAC

R:
(SEQ ID NO: 30)
CCCGAATTCTATTTACCCGGAGACAGGGAG wherein, HindIII and BamHI restriction enzyme recognition sites were added in the upstream primer for subsequent cloning, and an EcoRI restriction enzyme recognition site was added in the downstream primer.

Full length cDNA of PBMC was used as a template for amplification to obtain genes of an Fc fragment, then the obtained gene fragments were treated with double enzyme digestion with HindIII and BamHI from Takara company to be cloned into a modified vector pcDNA4m, and the accuracy of the constructed plasmid was verified by sequencing so as to obtain a recombinant plasmid pcDNA4m-Fc.

4. Construction of HER2 Variant Protein Eukaryotic Expression Vector

Primers are designed based on DNA sequence information (NM_004448.2) of a HER2 protein from NCBI to clone the extracellular domain (amino acid residues of position 1-652) of a wild type HER2 protein, and the primers used are as follows:

(SEQ ID NO: 31)
F: GCCAAGCTTGCCACCATGGAGCTGGCGGCCT (SEQ ID NO: 32)
R: CGCGGATCCATCGTCAGAGGGCTGGCTCTC

The primers contain upstream HindIII recognition sites and downstream BamHI recognition sites. cDNA of a BT474 cell (purchased from Shanghai Cell Bank of Chinese Academy of Sciences) were used as a template for amplification to obtain a 1.9 kb DNA fragment, encoding the extracellular domain of HER2 wt, it was cloned into a commercial T vector (pMD19-T Simple Vector purchased from Takara company) to obtain a T-Her2ECD plasmid, and the accuracy of the sequences was confirmed by sequencing.

Based on the amino acid sequences of the foregoing HER2 variant protein HER2 m1 recognized only by Trastuzumab, HER2 variant proteins HER2m2 and HER2m3 recognized only by Pertuzumab, corresponding primers were designed according to the mutation sites:

M1-F:
(SEQ ID NO: 33)
GCACCCTCGTCTGCCCCCTGGCTAACCAAGAGG

M1-R:
(SEQ ID NO: 34)
GGGGGCAGACGAGGGTGCAAGCTCCCACGT

M2-1-F:
(SEQ ID NO: 35)
GGACCGGCGGCTGACCA

M2-1-R:
(SEQ ID NO: 36)
TGGTCAGCCGCCGGTCC

M2-2-F:
(SEQ ID NO: 37)
TATAAGGACCCTGCCTTCTGCG

M2-2-R:
(SEQ ID NO: 38)
CGCAGAAGGCAGGGTCCTTAT

M3-F:
(SEQ ID NO: 39)
CTATAAGGACGCTGCCTTCTGCG

M3-R:
(SEQ ID NO: 40)
CGCAGAAGGCAGCGTCCTTATAG

Using the plasmid T-Her2ECD as a template, site-specific mutagenesis was carried out with the above primers to obtain genes of the three variant proteins (HER2m1, HER2m2, HER2m3) of HER2 extracellular domain. Then, they were treated with double enzyme digestion using HindIII and BamHI from Takara company and cloned into the vector pcDNA4m-Fc, the three genes HER2m1, HER2m2 and HER2m3 were fused to the 5' terminal of the Fc gene respectively, to obtain three new vectors named as pcDNA4m-Her2m1-Fc, pcDNA4m-Her2m2-Fc and pcDNA4m-Her2m3-Fc. These three vectors can be used for expressing fusion proteins HER2 m1-Fc, HER2m2-Fc and HER2m3-Fc in a mammalian cell.

5. Transient Expression and Purification of HER2 Variant Protein

Two days before transfection, 200 mL×3 of HEK293 (ATCC, CRL-1573™) cell suspension was prepared for transient transfection, and an inoculation density was 0.8× $10^6$ cells/mL. Two days later, cells in the suspension to be transfected were counted, and the cell density was determined to be 3.5-4×$10^6$ cells/mL, the cell suspension was centrifuged at 1000 rpm for 5 min, and the supernatant was discarded. Cells were resuspended with 40 mL×3 fresh Freestyle293 culture medium and then centrifuged again at 1000 rpm for 5 min, and the supernatant was discarded. 293 cells were suspended again with 200 mL×3 Freestyle293 culture medium. 200 μg of each of th expression vectors of the three HER2 variant proteins obtained in the examples 2-4 were diluted using 2 mL Freestyle293 culture medium, respectively. Subsequently, 1.5 mL Polyethylenimine was diluted using 5 mL Freestyle293 culture medium, and a PEI solution required for transformation was prepared. 2 mL PEI solution was respectively added into 2 mL diluted expression plasmids, fully mixed, and kept at room temperature for 5 min. Three parts of plasmid/PEI mixtures were respectively added into three parts of 200 mL cell suspensions, and cultured under 37° C., 10% CO, and 90 rpm; simultaneously, 50 μg/L IGF-1 was added. Four hours later, 200 mL EX293 culture medium, 2 mM Glutamine and 50 μg/L IGF-1 were further added into each part of the transformed samples, and cultured with 135 rpm. 24 hours later, 3.8 mM VPA was added.

Figure 4:
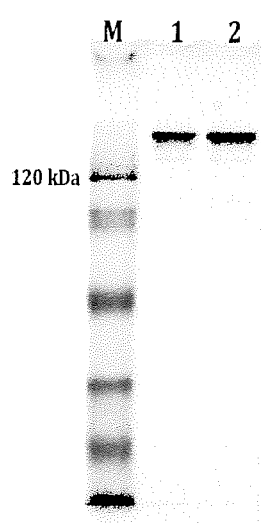
FIG. 4 illustrates an SDS-PAGE electrophoretic analysis result of Her2 m1 and Herm2 variant proteins (18% SDS-PAGE non-reduced condition).
1: HER2 m1; 2: HER2m2; M: protein MW standard.

After culturing for 5-6 days, three parts of 400 mL HER2 variant protein cell transient expression culture supernatant was collected respectively, and preliminarily purified by ProteinA affinity chromatography to obtain HER2 variant protein samples. Wherein, the expression level of HER2m3 was very low, and the titer of the template protein in the cell culture supernatant of HER2m3 was less than 0.5 mg/L, it was suspected that this might result from instability of the variant protein, and thus this protein was not further purified. The expression levels of the obtained HER2m1 and HER2m2 variant proteins were calculated to be about 20 mg/L after purification. The obtained protein samples were preliminarily examined with SDS-PAGE, and target bands were clearly seen (see FIG. 4).

6. Detection of specific binding of HER2 variant protein to Trastuzumab or Pertuzumab with ELISA An ELISA plate was coated with a Trastuzumab protein or a Pertuzumab protein at 4° C. overnight, then 3% BSA solution was added, and it was blocked at room temperature for 2 hours. The sample (HER2m1 or HER2m2 protein) was labeled with biotin in advance, and then the biotinylated proteins HER2m1-Biotin and HER2m2-Biotin were gradient-diluted in 1:4, starting from 16 μg/mL and till 0.224 ng/μL, including 9 gradients totally. The gradient-diluted biotinylated HER2 variant protein samples were added into the ELISA plate, and the reaction was allowed at room temperature for 2 hours. Then, HRP-labeled streptavidin was added, and the reaction was allowed at room temperature for 1.5 hours, and finally, the substrate was catalyzed for color development and the results were obtained. Affinity curves were obtained by fitting of data obtained using a four-parameter method.

Figure 5:
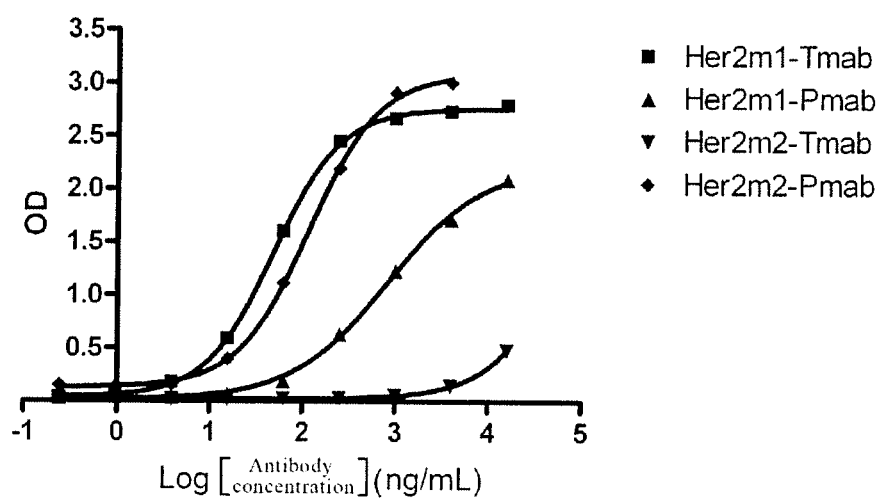
FIG. 5 illustrates detection of specific binding of a HER2 variant protein with Trastuzumab or Pertuzumab using ELISA.

As shown in FIG. 5, the apparent affinity of the HER2m1 protein to Pertuzumab was reduced by 20 times compared to that of the HER2m1 protein to Trastuzumab. Thus, it can be concluded that the variant protein is a Trastuzumab specific antigen protein. On the other hand, the apparent affinity of the HER2m2 protein to Pertuzumab was reduced by more than 2 orders of magnitude compared to that of the HER2m2 protein to Trastuzumab, showing that this variant protein is a Pertuzumab specific antigen protein.

Example 4 Replacement of the Original Light Chains of Tmab and Pmab with the Common Light Chain and Verification of the Effects of the Common Light Chain 1. Construction of Eukaryotic Expression Vectors of Tmab and Pmab Monoclonal Antibody Carrying Common Light Chains Corresponding encoding DNA sequences were designed using DNAworks on-line tool in accordance with amino acid sequences (FIG. 2 and FIG. 16 in the corresponding patent) of Trastuzumab and Pertuzumab full-length antibodies found in patent US2009/0285837A1, and the heavy chain gene (SEQ ID NO: 16) of Trastuzumab and the heavy chain gene (SEQ ID NO: 17) of Pertuzumab were obtained by an artificial synthesis. In accordance with the amino acid sequences (SEQ ID NO: 1-6) of a group of common light chains obtained in example 1, corresponding DNA sequences were designed using the DNAworks on-line tool, and the gene CLC1 (SEQ ID NO: 7) of the common light chain of the Pmab-Tmab bispecific antibody and the gene CLC5 (SEQ ID NO: 11) of the common light chain of the Pmab-Tmab bispecific antibody were obtained by artificial synthesis.

Then mutation primers were designed in accordance with the sequences of CLC2-CLC6, and the sequences were as follows:

T311-F:
GACGTGAACATTGCCGTTGC          (SEQ ID NO: 41)

T311-R:
GCAACGGCAATGTTCACGTC          (SEQ ID NO: 42)

T94Y-F:
AGCACTATACTTATCCTCCAACATTC    (SEQ ID NO: 43)

T94Y-R:
ATGTTGGAGGATAAGTATAGTGCTG     (SEQ ID NO: 44)

Y94T-F:
TCGCCACCACTTATTGTCAG          (SEQ ID NO: 45)

Y94T-R:
CTGACAATAAGTGGTGGCGA          (SEQ ID NO: 46)

Using the CLC1 gene as a template, sequences of CLC2-CLC4 (SEQ ID NO: 8-SEQ ID NO: 10) were obtained by site-directed mutagenesis using the two pairs of primers T31I and T94Y; using CLC5 as a template, the sequence of CLC6 (SEQ ID NO: 12) was obtained by site-directed mutagenesis using the Y94T primer pair.

The synthesized Trastuzumab heavy chain genes, the Pertuzumab heavy chain genes and the common light chain genes (CLC1-CLC6) were respectively subcloned into the modified vector pcDNA4m using double enzyme digestion with HindIII and EcoRI from Takara company, the accuracy of plasmid construction was verified by sequencing to obtain recombinant plasmid DNA, namely pcDNA4m-TmabHC, pcDNA4m-PmabHC and the common light chain related vectors pcDNA4m-CLC1 to pcDNA4m-CLC6.

The above successfully constructed common light chain gene expression vectors pcDNA4m-CLC1 to pcDNA4m-CLC6 were treated double enzyme digestion using Bgl II and Pvu II from Takara company. Enzyme-digested products were separated and purified using 0.8% agarose electrophoresis, and about 2 kb DNA fragments containing the common gene were respectively recovered; pcDNA4m-TmabHC was treated with double enzyme digestion using BglII and NruI to recover DNA fragments of about 6 kb containing TmabHC genes. pcDNA4m-PmabHC was treated with double enzyme digestion using BglII and NruI to recover DNA fragments of about 6 kb containing PmabHC genes. Subsequently, the DNA fragments treated by enzyme digestion were ligated, and expression elements of TmabHC or PmabHC were combined with common light chain expression elements of various sequences to obtain the recombinant plasmids pcDNA4m-Tmab-CLC1, pcDNA4m-Tmab-CLC2, pcDNA4m-Tmab-CLC3, pcDNA4m-Tmab-CLC4, pcDNA4m-Tmab-CLC5, pcDNA4m-Tmab-CLC6, pcDNA4m-Pmab-CLC1, pcDNA4m-Pmab-CLC2, pcDNA4m-Pmab-CLC3, pcDNA4m-Pmab-CLC4, pcDNA4m-Pmab-CLC5 and pcDNA4m-Pmab-CLC6.

2. Transient Expression and Purification of Tmab and Pmab Monoclonal Antibodies Carrying the Common Light Chains Two days before transfection, 50 mL×12 HEK293 (ATCC, CRL-1573™) cell suspensions were prepared for transient transfection, and an inoculation density was 0.8×10$^6$ cells/mL. Two days later, cells in the suspension to be transfected were counted to and the cell density was 3.5-4×10$^6$ cells/mL, the cell suspension was centrifuged for 5 min at 1000 rpm, and a supernatant was discarded. Cells were resuspended with a 10 mL×12 fresh Freestyle293 culture medium and then centrifuged again at 1000 rpm for 5 min, and the supernatant was discarded. 293 cells were resuspended with 50 mL×12 Freestyle293 culture medium. 50 μg of each of the 12 common light chain monoclonal antibody related expression vectors obtained in the examples 4-1 were diluted using 0.5 mL Freestyle293 culture medium respectively. Subsequently, 1.5 mL Polyethylenimine was diluted using 5 mL Freestyle293 culture medium, and PEI solution required for transformation was prepared. 0.5 mL PEI solution was respectively added into 0.5 mL diluted expression plasmids respectively, fully mixed, and kept at room temperature for 5 min. 12 parts of plasmid/PEI mixtures were respectively added into 12 parts of 50 mL cell suspensions to be cultured under 37° C., 10% CO, and 90 rpm; 50 μg/L IGF-1 was also added. Four hours later, 50 mL EX293 culture medium, 2 mM Glutamine and 50 μg/L IGF-1 were further added in each part of the transformed samples, and cultured with 135 rpm. 24 hours later, 3.8 mM VPA was added.

After culturing for 5-6 days, 12 parts of 100 mL supernatant of transient expression culture of common light chain monoclonal antibody cells were respectively collected, and preliminarily purified using ProteinA affinity chromatography to obtain 12 common light chain monoclonal antibody protein samples: Tmab-CLC1 to 6 and Pmab-CLC1 to 6; the expression level of each monoclonal antibody obtained after purification was calculated and the result is shown in Table 6.

Figure 6:
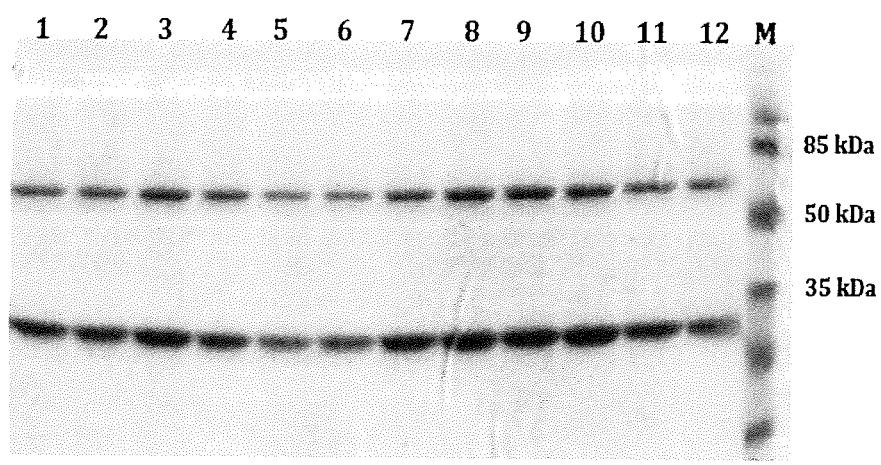
FIG. 6 is a reduced SDS-PAGE (12% SDS-PAGE reduced condition) result showing primary detection of a common light chain monoclonal antibody protein sample obtained by one-step affinity chromatographic purification.
1-6: TmabCLC1-6; 7-12: PmabCLC1-6; M: protein MW standard.

Protein samples obtained by one-step affinity chromatography purification were preliminarily detected using non-reduced SDS-PAGE. As shown in FIG. 6, two clear bands can be seen for each of the common light chain monoclonal antibody protein on the reduced gel, which were respectively a light chain band between 25 kDa and 35 kDa and a heavy chain band between 85 kDa and 50 kDa. The purities of the protein samples were examined using SE-HPLC and the results are shown in Table 6.

TABLE 6

Transient expression level of common light chain monoclonal antibody and sample purity after one-step purification

| Common light chain monoclonal antibody sample | Expression level (mg/L) | Sample purity (%) |
|---|---|---|
| TmabCLC1 | 56 | 98.7 |
| TmabCLC2 | 28 | 98.8 |
| TmabCLC3 | 38 | 98.7 |
| TmabCLC4 | 56 | 96.4 |
| TmabCLC5 | 25 | 95.2 |
| TmabCLC6 | 38 | 96.1 |
| PmabCLC1 | 48 | 95.7 |
| PmabCLC2 | 50 | 96.8 |
| PmabCLC3 | 51 | 96.9 |
| PmabCLC4 | 46 | 98.9 |
| PmabCLC5 | 40 | 98.7 |
| PmabCLC6 | 42 | 98.9 |

Figure 7:
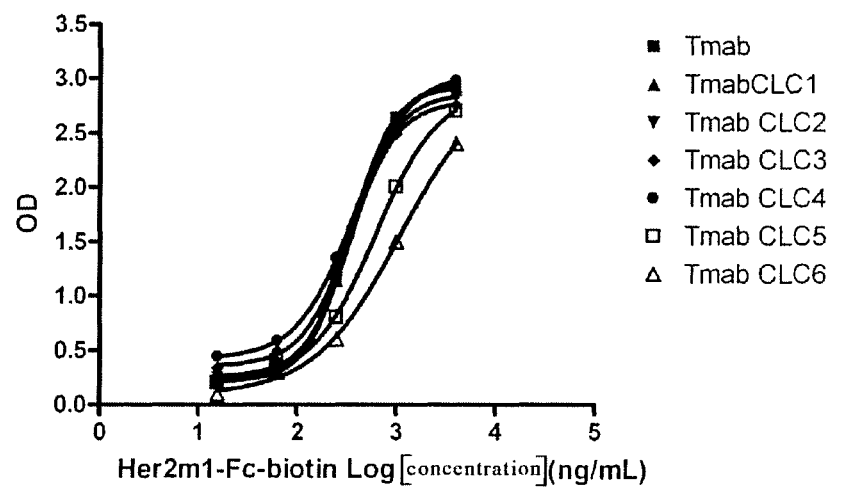
FIG. 7 illustrates affinity of Trastuzumab comprising the common light chain to its specific antigen HER2 m1.
Figure 8:
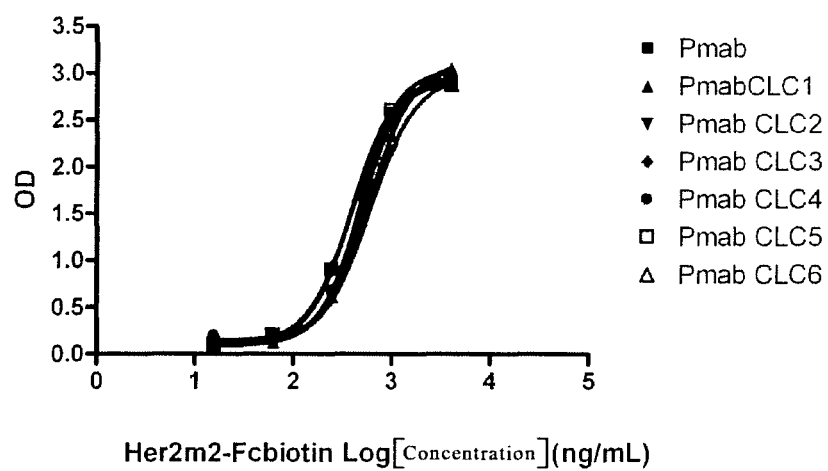
FIG. 8 illustrates affinity of Pertuzumab comprising a common light chain to its specific antigen HER2m2.

3. Analyzing the Affinity of Tmab and Pmab Comprising the Common Light Chains with ELISA Changes in affinity of Tratuzumab and Pertuzumab comprising the common light chains with their respective specific antigens were examined, and the indirect ELISA method used was similar to that in examples 2-6. Wherein, when changes in the affinity of Tratuzumab comprising the common light chains were examined, the specific antigen protein HER2m1 was used; and when changes in the affinity of Pertuzumab comprising the common light chains were examined, the specific antigen protein HER2m2 was used. The affinity curves obtained were shown in FIGS. 7-8. According to EC50, when the common light chains (CLC1-CLC4) obtained by modifying the light chains of the original Tratuzumab were used, the affinity of Tratuzumab with its specific antigen HER2m1 was not changed in any significant way; while the affinity of Pertuzumab with its specific antigen HER2m2 was slightly reduced, but this change was in an acceptable range. However, when the common light chains (CLC5 and CLC6) obtained by modifying the light chains of the original Pertuzumab were used, the affinity of Pertuzumab with its specific antigen HER2m2 was not changed in any significant way, but the affinity of Tratuzumab with its specific antigen HER2m1 was reduced by nearly one-fold.

Example 5 Preparation and Identification of Ptmab Bispecific Antibody

1. Transient Expression and Purification of Ptmab Bispecific Antibody

Point mutations were introduced in Fc fragment of TmabHC in pcDNA4m-Tmab-CLC1, and TmabHC was changed to TmabHC-knob (its heavy chain sequence was as set forth in SEQ ID NO: 19; the mutated residues were S354C and T366W), and pcDNA4m-Tmabknob-CLC1 was further constructed; meanwhile, amino acid residues in PmabHC of pcDNA4m-Pmab-CLC1 were mutated into PmabHC-hole (its heavy chain sequence was as set forth in SEQ ID NO: 20; the mutated residues were Y349C, T366S, L368A and Y407V) using site-directed mutagenesis referring to patent CN102558355A, and pcDNA4m-Pmabhole-CLC1 was further constructed. CN102558355A was referred to for specific mutation schemes. These two newly constructed plasmids will be used to prepare the Pmab-Tmab bispecific antibody with a common light chain model, based on the "knob-hole" model.

2. Transient Expression and Purification of Ptmab Bispecific Antibody

Two days before transfection, 600 mL of HEK293 (ATCC, CRL-1573™) cell suspension was prepared for transient transfection, and an inoculation density was $0.8 \times 10^6$ cells/mL. Two days later, cells in the suspension to be transfected were counted, and the cell density was $3.5\text{-}4 \times 10^6$ cells/mL, the cell suspension was centrifuged at 1000 rpm for 5 min, and the supernatant was discarded. Cells were resuspended with 100 mL fresh Freestyle293 culture medium and then centrifuged again at 1000 rpm for 5 min, and the supernatant was discarded. 293 cells were resuspended with a 600 mL Freestyle293 culture medium. 300 µg of each of pcDNA4m-Tmabknob-CLC1 and pcDNA4M-Pmabhole-CLC1 was fully mixed, and then diluted using 3 mL Freestyle293 culture medium respectively. Subsequently, 1.5 mL Polyethylenimine was diluted using 5 mL Freestyle293 culture medium, and PEI solution required for transformation was prepared. 3 mL PEI solution was added in 3 mL diluted mixed plasmids, fully mixed, and kept at room temperature for 5 min. The plasmid/PEI mixture was added in 600 mL cell suspensions, and cultured under 37° C., 10% $CO_2$ and 90 rpm; 50 µg/L IGF-1 was added as well. Four hours later, 600 mL EX293 culture medium, 2 mM Glutamine and 50 µg/L IGF-1 were added in the transformed samples again, and cultured with 135 rpm. 24 hours later, 3.8 mM VPA was added.

After culturing for 6-7 days, 1200 mL supernatant of transient expression culture of Ptmab bispecific antibody cell, and then preliminarily purified using ProteinA affinity chromatography, ion-exchange chromatography and molecular sieve chromatography to obtain a Ptmab bispecific protein sample named KN026. A transient expression level of KN026 was as high as 80 mg/L, according to the calculation using OD280.

Figure 9:
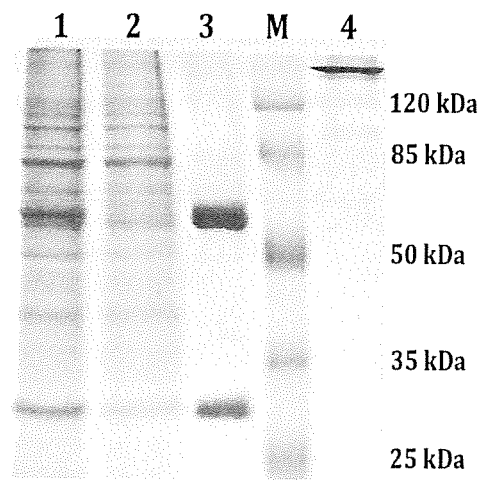
FIG. 9 is an SDS-PAGE (12% SDS-PAGE reduced condition) result showing primary detection of a KN026 antibody protein sample obtained by one-step affinity chromatographic purification.
1: KN026 transient expression cell culture supernatant; 2: KN026 affinity chromatography flow through; 3: purified protein sample (reduction) after KN026 one-step affinity chromatography; 4: purified protein sample (non-reduced) after KN026 one-step affinity chromatography; M: protein MW standard.
Figure 10:
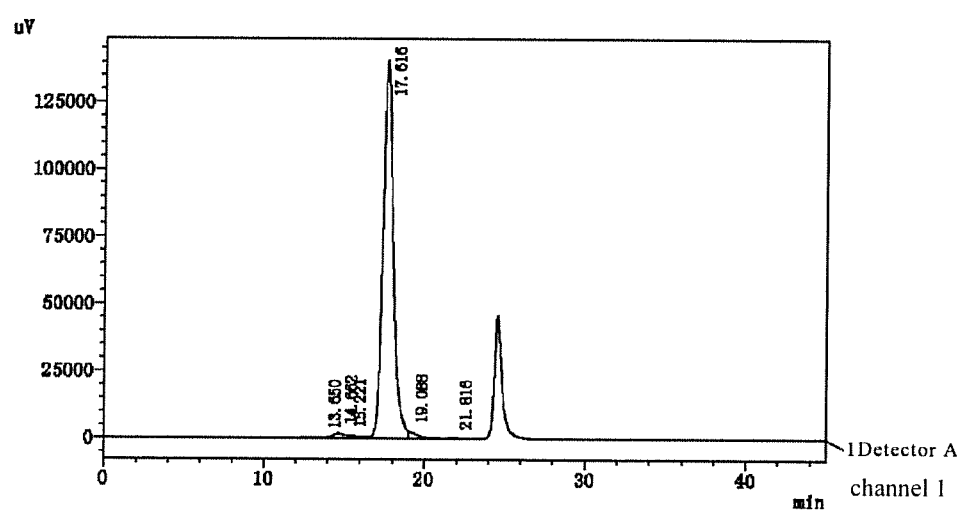
FIG. 10 illustrates an SE-HPLC detection result of KN026 antibody protein purity.

The protein sample obtained after purification was preliminarily examined with SDS-PAGE. As shown in FIG. 9, two clear bands of the KN026 bispecific antibody protein can be seen on the reduced gel, which were respectively a light chain band between 25 kDa and 35 kaDa and a heavy chain band between 85 kDa and 50 kDa. Meanwhile, under the non-reduced conditions, KN026 was shown as a single band. The purity of the protein sample was examined using SE-HPLC and it was about 95%, the result was shown in FIG. 10.

3. Verification of the Ability of KN026 Antibody Protein to Simultaneously Recognize the Corresponding Specific Antigens of Trastuzumab and Pertuzumab with Bridging ELISA An ELISA plate was coated with Trastuzumab specific antigen protein HER2m1 at 4° C. overnight. Then, 3% BSA solution was added, and it was blocked at room temperature for 2 hours. The sample to be tested was gradient-diluted at 1:3, starting from 5 µg/mL to 1.06 ng/µL, including 8 gradients in total. The sample after gradient dilution was added into the ELISA plate, and the reaction was allowed at room temperature for 2 hours. Then, biotinylated Pertuzumab specific antigen protein HER2m2-Biotin was added into the ELISA plate to react with the sample for 2 hours. Subsequently, HRP labeled streptavidin was added to react with HER2m2-Biotin for 1.5 hours at room temperature, and finally, the substrate was catalyzed for color development and the results were obtained. Affinity curves were obtained after fitting of the data obtained, using the four-parameter method.

Figure 11:
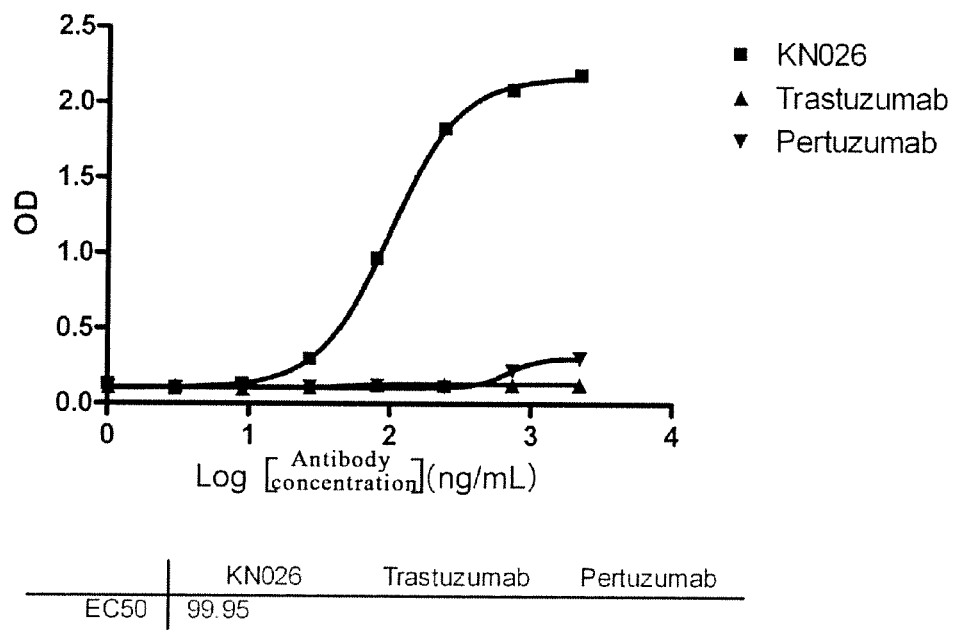
FIG. 11 illustrates affinity curves showing recognition of two antigens by bispecific antibody KN026.

As shown in FIG. 11, only the bispecific antibody KN026 capable of simultaneously recognizing two antigens can provide an affinity curve, while for Trastuzumab or Pertuzumab capable of specifically recognizing only one antigen, clearly developed color could not be seen even at the highest concentration.

Example 6 Preparation and Identification of Ptmab Antibody Mixture

1. Transient Expression and Purification of Ptmab Antibody Mixture

Point mutations were introduced in Fc fragment of TmabHC in pcDNA4m-Tmab-CLC1, and TmabHC was changed to TmabHC-mix1 (wherein the heavy chain sequence was as set forth in SEQ ID NO: 21), and pcDNA4m-Tmabmix1-CLC1 was further constructed, Example 1 of patent CN103388013A was referred to for specific construction steps. Based on the "charge repulsion" mixture model while using the common light chain model, these two newly constructed plasmids were used to prepare a Pmab and Tmab antibody mixture capable of being expressed in a single recombinant cell strain.

2. Transient Expression and Purification of Pmab and Tmab Antibody Mixture

Two days before transfection, 600 mL HEK293 (ATCC, CRL-1573™) cell suspension was prepared for transient transfection, and an inoculum density was $0.8 \times 10^6$ cells/mL. Two days later, cells in the suspension to be transfected were counted, and the cell density was $3.5-4 \times 10^6$ cells/mL, the cell suspension was centrifuged at 1000 rpm for 5 min, and the supernatant was discarded. Cells were resuspended with 100 mL fresh Freestyle293 culture medium and then centrifuged again at 1000 rpm for 5 min, and the supernatant was discarded. 293 cells were resuspended in 600 mL Freestyle293 culture medium. 300 μg of each of pcDNA4m-Tmabkmix1-CLC1 and pcDNA4m-Pmab-CLC1 (wherein the heavy chain sequence was as set forth in SEQ ID NO: 22) were fully mixed, and then diluted using 3 mL Freestyle293 culture medium. Subsequently, 1.5 mL Polyethylenimine was diluted using 5 mL Freestyle293 culture medium, and PEI solution required for transformation was prepared. 3 mL PEI solution was added into 3 mL diluted mixed plasmid, fully mixed, and kept at room temperature for 5 min. The plasmid/PEI mixture was added in 600 mL cell suspension, and cultured under 37° C., 10% CO, and 90 rpm; meanwhile, 50 μg/L IGF-1 was added. Four hours later, 600 mL EX293 culture medium, 2 mM Glutamine and 50 μg/L IGF-1 were added in the transformed samples again, and cultured with 135 rpm. 24 hours later, 3.8 mM VPA was added.

After culturing for 6-7 days, 1200 mL supernatant of transient expression culture of Ptmab and Tmab antibody mixture cell was collected, and then preliminarily purified using ProteinA affinity chromatography to obtain a Ptmab and Tmab antibody mixture protein sample, named as KN010. The transient expression level of KN010 was calculated to be as high as 100 mg/L, according to the OD280 measurement.

Figure 12:
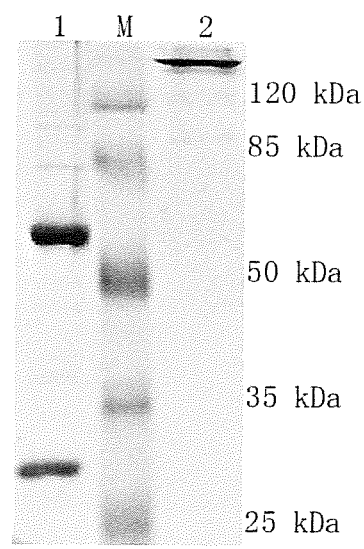
FIG. 12 is an SDS-PAGE (12% SDS-PAGE reduced condition) result showing primary detection of a KN010 antibody protein sample obtained by one-step affinity chromatographic purification.
Figure 13:
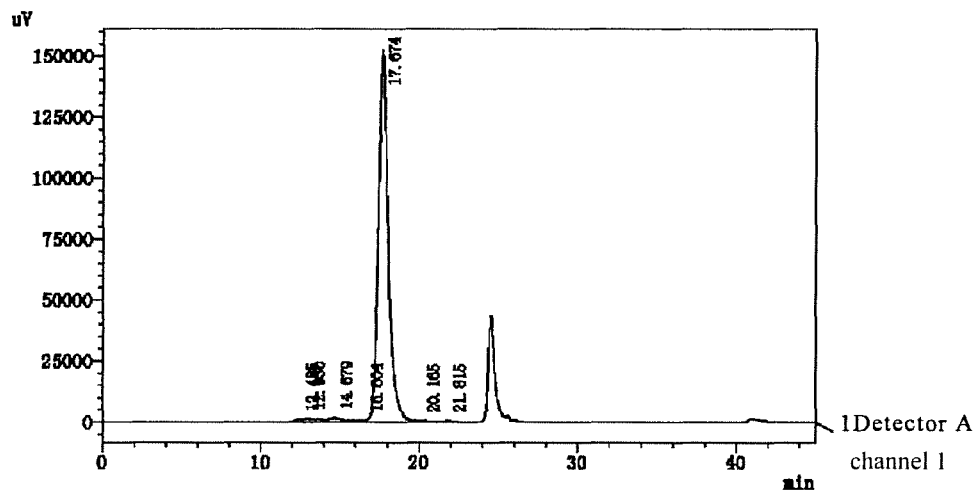
FIG. 13 illustrates an SE-HPLC detection result of mixed antibody protein KN026.

The protein sample obtained by one-step affinity chromatography purification was preliminarily examined with SDS-PAGE. As shown in FIG. 12, two clear bands of the common light chain monoclonal antibody mixture protein product can be seen on the reduced gel, which were a light chain band between 25 kDa and 35 kDa and a heavy chain band between 85 kDa and 50 kDa. Meanwhile, under the non-reduced condition, KN010 was shown as a single band. The purity of the protein sample was examined using SE-HPLC and the purity was about 95%, the results are shown in FIG. 13.

3. The Ability of KN010 to Recognize the Corresponding Specific Antigens of Trastuzumab and Pertuzumab was Verified Using Bridging ELISA with the Same Antigen; it was Verified that KN010 was Incapable of Simultaneously Recognizing this Pair of Antigens Using Bridging ELISA with Different Antigens.

An ELISA plate was coated with Trastuzumab specific antigen protein HER2m1 at 4° C. overnight. Then, 3% BSA solution was added, and it was blocked for 2 hours at room temperature. A sample to be examined was gradient-diluted in 1:4, starting from 2.5 μg/mL until 0.61 ng/μL, including 7 gradients in total. The sample to be examined after gradient dilution was added in the ELISA plate, and the reaction was allowed at room temperature for 2 hours. Then, biotinylated Pertuzumab specific antigen protein HER2m2-Biotin or biotinylated HER2m1-Biotin was added to the ELISA plate to react with the sample to be examined at room temperature for 2 hours. Subsequently, HRP-labeled streptavidin was added to react with HER2m2-Biotin or HER2m1-Biotin at room temperature for 1.5 hours, and finally the substrate was catalyzed for color development and the results were obtained. Affinity curves were obtained by fitting of the data obtained using the four-parameter method.

An ELISA plate was coated with Perstuzumab specific antigen protein HER2m2 at 4° C. overnight. Then, 3% BSA solution was added, and it was blocked at room temperature for 2 hours. A sample to be examined was gradient-diluted in 1:4, starting from 2.5 μg/mL until 0.61 ng/4, including 7 gradients in total. The sample to be examined after gradient dilution was added in the ELISA plate, and kept at room temperature for 2 hours. Then, biotinylated Pertuzumab specific antigen protein HER2m2-Biotin was added in the ELISA plate to react with the sample to be examined at room temperature for 2 hours. Subsequently, HRP-labeled streptavidin was added to react with HER2m2-Biotin at room temperature for 1.5 hours, and finally the substrate was catalyzed for color development and the results were obtained. Affinity curves were obtained by fitting of the data obtained using the four-parameter method.

Figure 14:
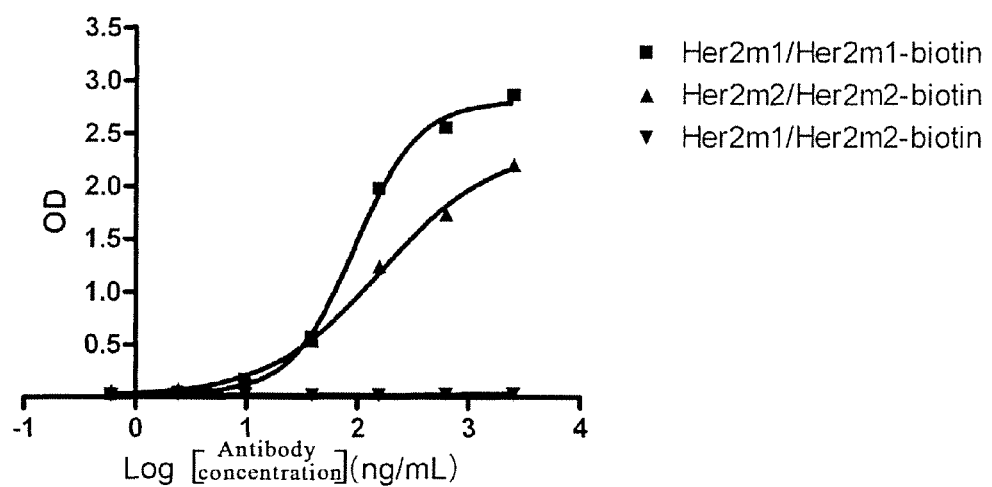
FIG. 14 illustrates affinity curves showing recognition of two antigens by the mixed antibody protein KN026.

As shown in FIG. 14, it was proved in the Bridging ELISA with the same antigen that the two arms of KN010 protein were capable of simultaneously recognizing the antigen of Trastuzumab, or simultaneously recognizing the antigen of Pertuzumab. It indicates that the KN010 protein at least comprises two antibodies capable of recognizing different antigen targets. However, color development was not observed using Bridging ELISA with different antigens, proving that the two arms of KN010 are incapable of simultaneously recognizing these two antigens, meaning that KN010 does not contain a Ptmab heterodimer component.

Example 7 Binding Activity of Ptmab Bispecific Antibody to Cell Surface HER2 Protein 1. Binding Activity of Ptmab Bispecific Antibody to Human Breast Cancer BT474 Cell Surface HER2 Protein Binding of HER2 over-expression breast cancer cell BT474 with HER2 antibodies (such as the Ptmab bispecific antibody, Pertuzumab and Trastuzumab) was examined using flow cytometry, and concentration dependency of the binding effects was also examined.

Figure 15:
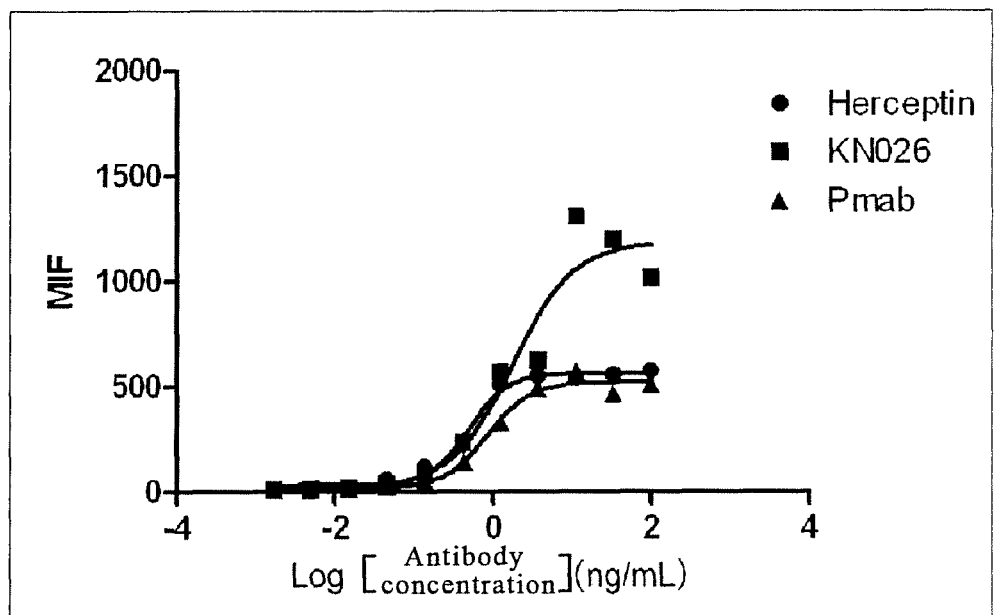
FIG. 15 illustrates concentration dependent curves of binding of Ptmab bispecific antibody (KN026), Pertuzumab and Trastuzumab with BT474 cells.

After digestion, BT474 cells were resuspended in 5% BSA/PBS, and $3 \times 10^5$ cells/tube were added into each 1.5 mL centrifuge tube; the samples to be examined were diluted by three-fold, starting from 100m/mL till 0.001694 μg/mL, including 11 concentrations in total. The samples were allowed to interact with the cells, then FITC-rabbit anti-human IgG was added to test binding of the antibodies to the cells, and the mean fluorescence intensity (MFI) was recorded using flow cytometry. Curves of MFI plotted against Logarithm values of antibody concentrations were made, and concentration dependency curves revealing binding of the antibodies to BT474 cells were obtained by fitting using the four-parameter method. As shown in FIG. 15, the Ptmab bispecific antibody (KN026) as well as Pertuzumab and Trastuzumab all clearly bound to BT474, and this effect was concentration dependent. As can be seen from EC50 of the binding curves, the affinity of KN026 to the BT474 cell surface HER2 protein was close to that of Trastuzumab.

2. Binding of Ptmab Bispecific Antibody to Human Gastric Cancer N-87 Cell Surface HER2 Protein Binding of HER2 over-expression gastric cancer cell N-87 with HER2 antibodies (such as a Ptmab bispecific antibody KN026, Pertuzumab and Trastuzumab) was examined using flow cytometry, and concentration dependency of the binding effects was examined as well.

Figure 16:
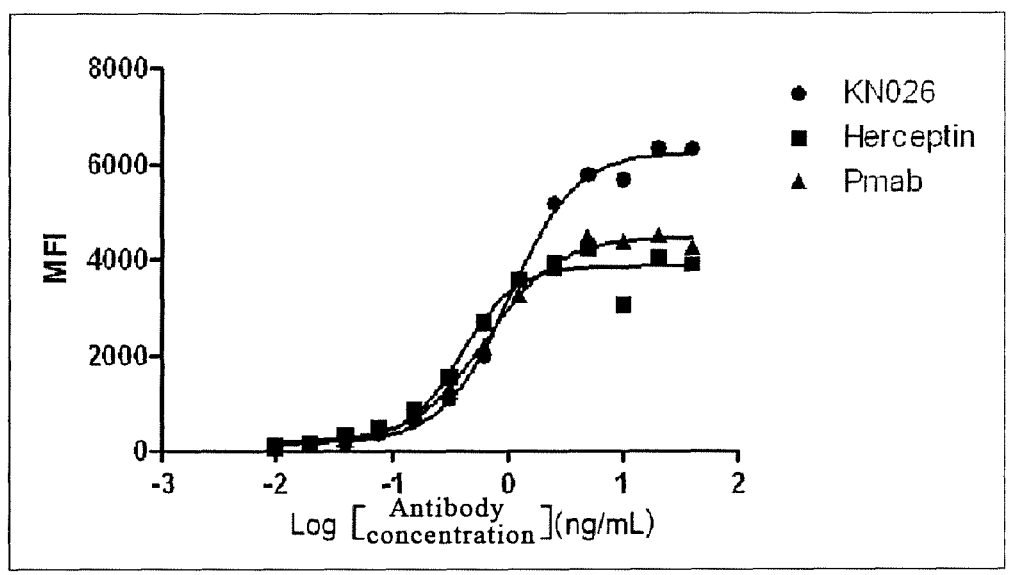
FIG. 16 illustrates concentration dependent curves of binding of Ptmab bispecific antibody (KN026), Pertuzumab and Trastuzumab with N-87 cells.

After digestion, N-87 cells were resuspended in 5% BSA/PBS, and 3×10⁵ cells/tube were added into each 1.5 mL centrifuge tube; the samples to be examined were diluted by two-fold, starting from 40 µg/mL till 0.009766 µg/mL, including 13 concentrations in total. The samples were allowed to react with cells, then FITC-rabbit anti-human human IgG was added to detect the antibodies bound to the cells, and a mean fluorescence intensity (MFI) was measured using flow cytometry. Curves of MFI plotted against logarithm values of antibody concentrations were made, and concentration dependency curves for the binding of the antibodies to BT474 cells were obtained by fitting using the four-parameter method. As shown in FIG. 16, the Ptmab bispecific antibody (KN026) as well as Pertuzumab and Trastuzumab all clearly bound to N-87, and the binding effect was concentration dependent. As can be seen from EC50 of the binding curves, the affinity of KN026 to the N-87 cell surface HER2 protein was slightly lower than that of Trastuzumab and Pertuzumab.

Example 8 Binding of Pmab and Tmab Antibody Mixture to Cell Surface Her2 Protein Binding Pmab and Tmab antibody mixture to human breast cancer BT474 cell surface HER2 protein Binding of HER2 over-expression breast cancer cell BT474 with HER2 antibodies (such as a mixture of Pmab and Tmab antibody, Pertuzumab and Trastuzumab) was examined using flow cytometry, and concentration dependency of the binding effects was also examined.

Figure 17:
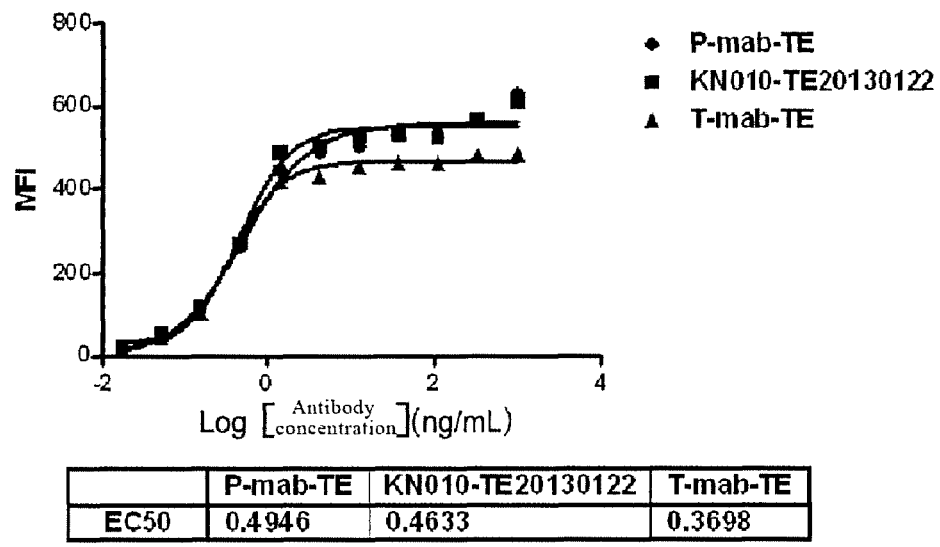
FIG. 17 illustrates concentration dependent curves of binding of Ptmab and Tmab antibody mixture (KN010), Pertuzumab and Trastuzumab with BT474 cells.

After digestion, BT474 cells were resuspended in 5% BSA/PBS, and 15×10⁶ cells/tube were added in each 1.5 mL centrifuge tube; the samples to be examined were diluted by three-fold, starting from 1000m/mL until 0.01694 µg/mL, including 11 concentrations in total. The samples were allowed to react with the cells, then FITC-rabbit anti-human was added to detect the antibodies bound to the cells, and a mean fluorescence intensity (MFI) was read using flow cytometry. Curves of MFI plotted against logarithm values of antibody concentrations were made, and concentration dependency curves of binding of the antibodies to the BT474 cells were obtained by fitting using the four-parameter method. As shown in FIG. 17, the mixture of Pmab and Tmab antibody (KN010) as well as Pertuzumab and Trastuzumab all clearly bound to BT474, and the binding effect was concentration dependent. As can be seen from EC50 of the curves, the affinity of KN010 to the BT474 cell surface HER2 protein is in between those of Trastuzumab and Pertuzumab.

Example 9 Inhibition of Ptmab Bispecific Antibody on Cancer Cell Proliferation

1. Inhibition of Ptmab Bispecific Antibody on Human Breast Cancer BT474 Cell Proliferation The CKK-8 method was used to examine changes in the proliferation of HER2 over-expression breast cancer cell BT474 in the presence of HER2 antibodies (such as a Ptmab bispecific antibody, Pertuzumab and Trastuzumab), thereby comparing and evaluating the inhibition effect of the Ptmab bispecific antibody on BT474 cancer cell proliferation.

BT474 cells were adherent-cultured in a 96-well plate at a density of 10000 cells/well and at 37° C. for 16h. Samples of various concentrations were prepared respectively using an assay medium (DMEM culture medium, supplemented with 1% fetal calf serum): a maximum concentration was 10 µm/ml-0.0015 µg/m, and diluted by 3-fold, including 9 concentrations in total. 150 µl samples were added in each cell well, and 72h later, cell vitality was measured with a CKK-8 kit (DOJNDO). The cell vitality was plotted against logarithm values of sample concentrations, and cell killing activity curves of the sample (Ptmab bispecific antibody KN026) and a reference (Trastuzumab and Trastuzumab+Pertuzumab combination) were obtained by fitting using the four-parameter method.

Figure 18:
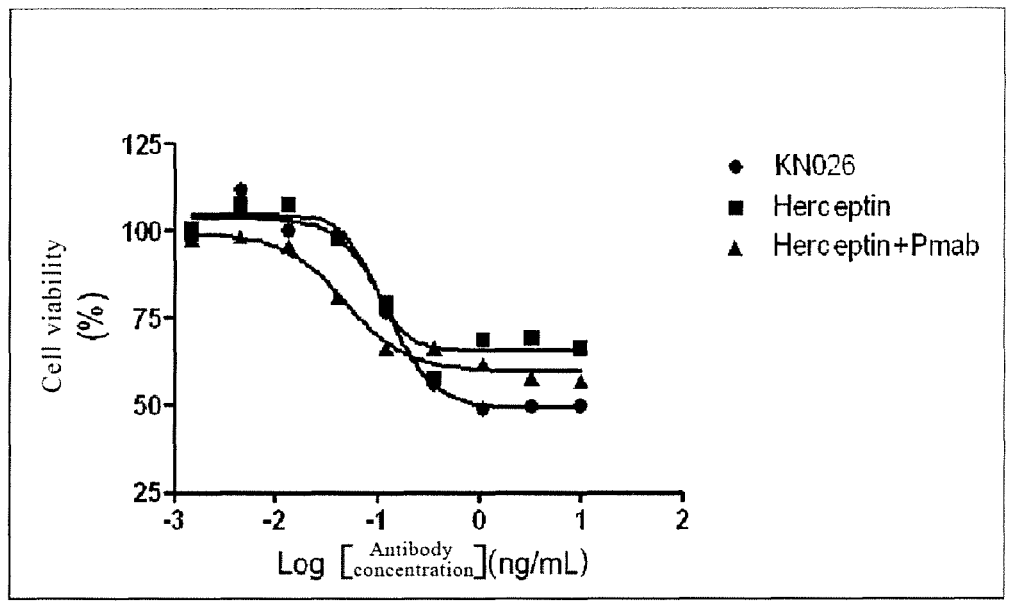
FIG. 18 illustrates inhibition effects of KN026, Trastuzumab and Trastuzumab+Pertuzumab drug combination on human breast cancer BT474 cell proliferation.

As shown in FIG. 18, KN026 and Trastuzumab as well as Trastuzumab+Pertuzumab combination all have a clear killing effect on BT474, and this killing effect was concentration dependent. However, at high concentration, the inhibition effect of the Ptmab bispecific antibody KN026 on BT474 cells was clearly superior to that of Trastuzumab alone or the combination of Pertuzumab and Trastuzumab.

2. Inhibition of Ptmab Bispecific Antibody on Human Gastric Cancer N-87 Cell Proliferation Changes in proliferation of HER2 over-expression gastric cancer cells N-87 in the presence of HER2 antibodies (such as a Ptmab bispecific antibody, Pertuzumab and Trastuzumab) were observed using a MTT method, thereby comparing and evaluating the inhibition effect of the Ptmab bispecific antibody on N-87 cancer cell proliferation.

N-87 cells were adherent cultured in a 96-well plate at a density of 10000 cells/well, at 37° C. for 16h. Samples of various concentrations were prepared respectively using an assay medium (RPMI-1640 medium, supplemented with 1% fetal calf serum): a maximum concentration was 10 µg/ml-0.0015 µg/m, and diluted by three-fold, including 9 concentrations in total. 150 µl samples were added in each cell well, and 72 h later, cell vitality was measured with a CKK-8 kit (DOJNDO). The cell vitality obtained was plotted against the logarithm values of sample concentrations, and cell killing curves of the sample (Ptmab bispecific antibody) and the reference (Trastuzumab and Trastuzumab+Pertuzumab combination) were obtained by fitting using the four-parameter method.

Figure 19:
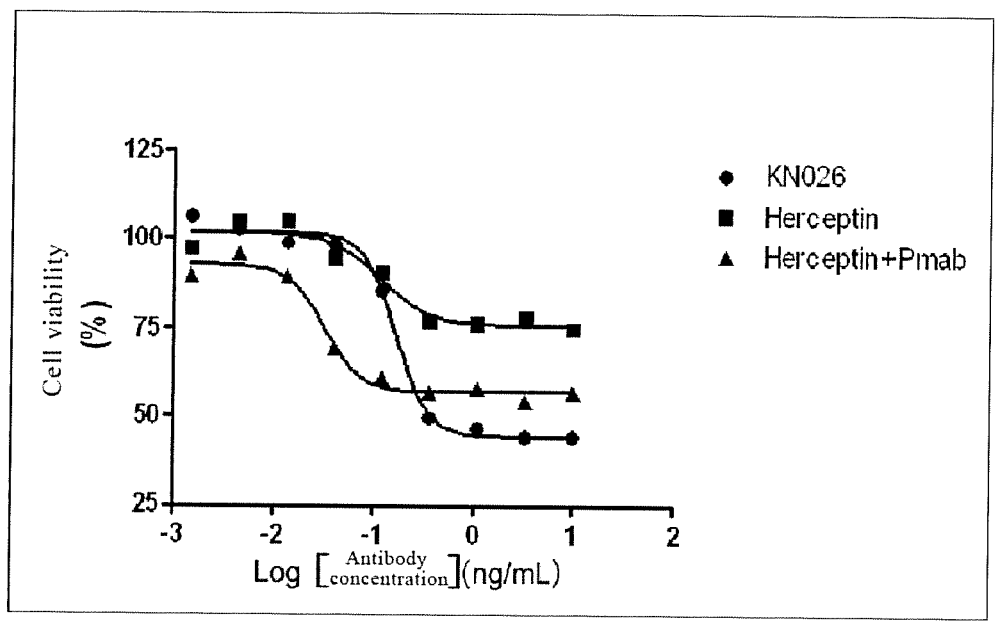
FIG. 19 illustrates inhibition effects of KN026, Trastuzumab and Trastuzumab+Pertuzumab drug combination on human gastric cancer N-87 cell proliferation.

As shown in FIG. 19, KN026 and Trastuzumab as well as Trastuzumab+Pertuzumab combination all have a clear killing effect on N-87, and this killing effect was concentration dependent. However, at high concentration, the inhibition effect of the bispecific antibody on N-87 is clearly superior to that of Trastuzumab alone or the combination of Pertuzumab and Trastuzumab.

Example 10 Evaluation of the Thermal Stability of Ptmab Bispecific Antibody

1. Measuring the Tm Value of Ptmab Bispecific Antibody

Tm values of a Ptmab bispecific antibody KN026 and a reference antibody (Trastuzumab was used as a reference sample herein) were measured by DSC (differential scanning calorimeter) method, and accordingly, the thermal stability of the Ptmab bispecific antibody was determined preliminarily.

The sample proteins were prepared at a concentration of 2 mg/mL in a 1×PBS buffer (pH7.4). The specific heat capacities (Cp) of the samples or blank buffer were scanned at a rate of 60° C./hr, starting from 10° C. The results of the corresponding buffer were deducted from the results obtained for the samples, the obtained Cp values were plotted against the temperature, wherein, the temperature corresponding to the peak value with clear increase of Cp is the Tm of the sample.

Figure 20:
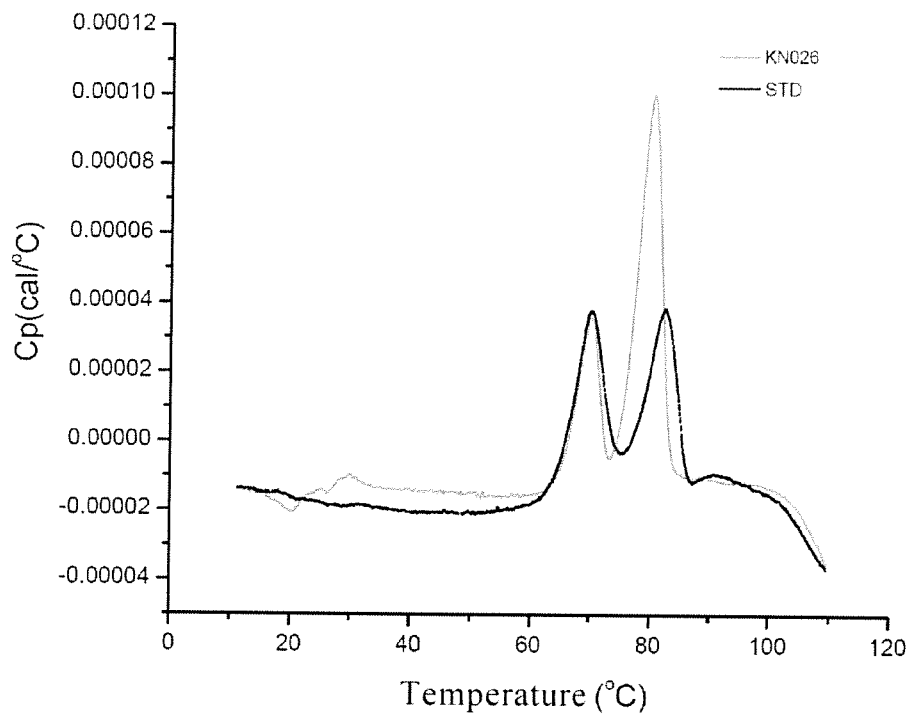
FIG. 20 illustrates thermal stability test results (Tm values) of a Ptmab bispecific antibody KN026 (light curve) and a Trastuzumab reference sample (dark curve).

As shown in FIG. 20, similar to a traditional antibody, both the Ptmab bispecific antibody KN026 and the Trastuzumab reference sample clearly showed two Tm values, including a CH2 disassemble temperature at about 60° C. and a CH3 disassemble temperature at about 80° C. Meanwhile, it can be seen that for the Tm value at about 60° C., there was no significant difference between the bispecific antibody and the Trastuzumab reference; for the Tm value at about 80° C., the bispecific antibody is slightly lower but is still higher than that at 80° C., and the difference to that of the reference was not significant, thus, shall not be considered to affect the thermal stability of the antibody.

Example 11 Pharmacokinetic Experiment in Mice Using Ptmab Bispecific Antibody

1. Examining the Metabolism of Ptmab Bispecific Antibodies in Mice 6 to 7-week old mice were selected, and divided into two groups randomly. The experiment group was intraperitoneally injected with 10 mg/kg Ptmab bispecific antibody KN026, and the reference group was intraperitoneally injected with 10 mg/kg of Trastuzumab reference sample. Each group was divided into three sub-groups, and blood samples were taken from four animals in each sub-group at different time points. During the experiment, at each time point (5 min-96h), 0.2 ml of blood was taken from the orbital venous plexus of each animal; at the end point (192h-576h), blood samples were taken from the postcava after euthanasia of the mice with isoflurane inhalation anesthesia. After the blood samples were collected, serums were separated and temporarily stored at −80° C.

Figure 21:
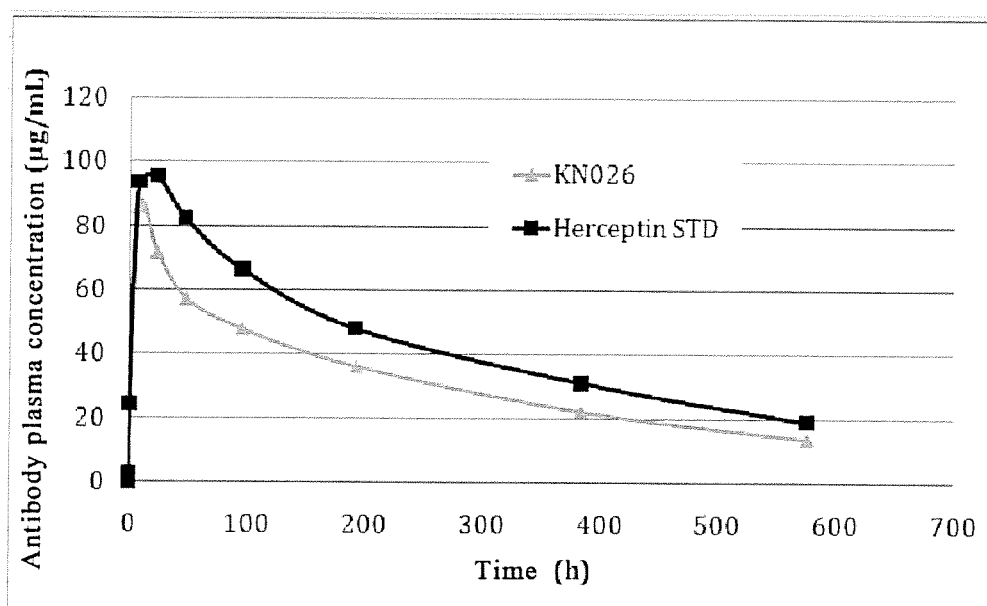
FIG. 21 illustrates pharmacokinetic curves of KN026 and Trastuzumab.

For the serum samples, blood concentration of the drugs was examined using Tmab and Ptmab specific ELISA, the detected amount of the antibodies in the serums was plotted against the sampling time to obtain pharmacokinetic curves of the bispecific antibody (KN026) and the reference antibody (Trastuzumab) (see FIG. 21), and corresponding Phannacokinetic parameters were further calculated (Table 7). As can be seen, the half-life of the Ptmab bispecific antibody (KN026) in mice was slightly lower than that of Trastuzumab, but was still longer than 10 days, and similar to the half-life of most monoclonal antibodies in mice, thus, it can be concluded that the stability of Ptmab in mice is similar to that of conventional monoclonal antibodies.

the tumor was measured twice each week. 20 mg/kg of Ptmab bispecific antibody KN026 was administered to the experiment group each time, 20 mg/kg of Trastuzumab reference sample or Pertuzumab reference sample was administered to the reference group each time, and the same volume of PBS buffer was administered to a blank control group each time.

Figure 22:
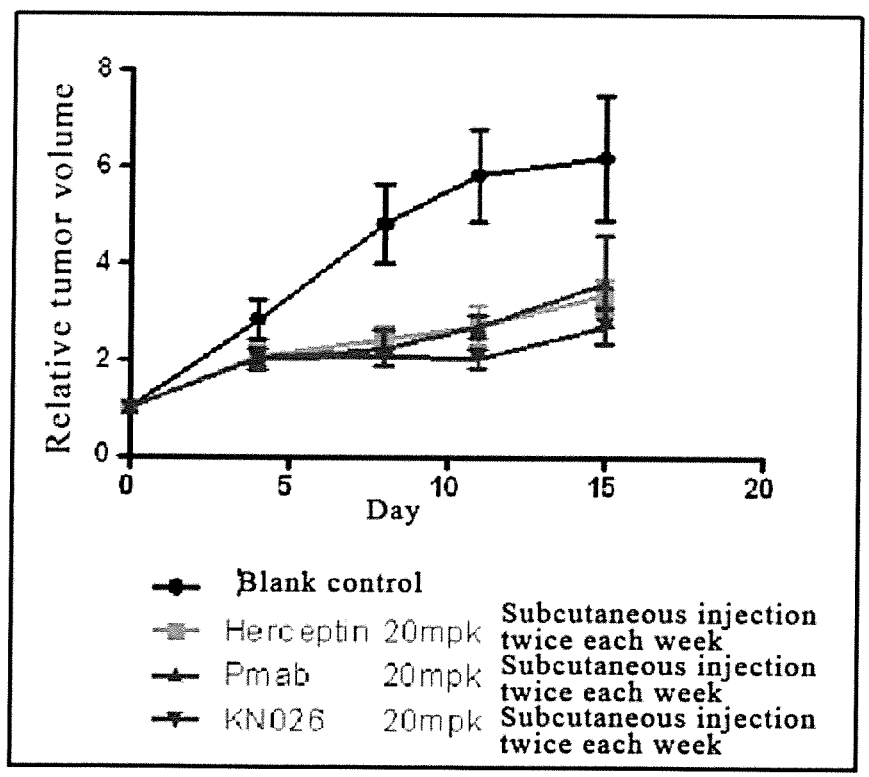
FIG. 22 illustrates influence of a Ptmab bispecific antibody on the tumor size of a human ovarian cancer SKOV3 nude mouse xenograft.

As shown in FIG. 22, comparing to the blank control group, both the experiment group and the reference group showed some tumor inhibition effect on the SKOV3 nude-mouse xenograft model, wherein the Ptmab bispecific antibody showed a stronger tumor inhibition effect than that of the Trastuzumab reference sample alone or the Pertuzumab reference sample alone.

Example 13 Pharmacodynamic Effect of Ptmab Bispecific Antibody on Human Gastric Cancer N-87 Nude-Mouse Xenograft Model Balb/c nude mice were subcutaneously inoculated with human gastric cancer N-87 cells at a dosage of $4 \times 10^6$ cells/mouse, and tumor-bearing mice were grouped randomly with 6 mice in each group (half of them were males and the other half were females). When the tumor grew to a volume of about 100-130 mm$^3$, a tumor-inhibiting drug was injected by IP administration twice per week for 4-5 consecutive weeks. The size of tumor was measured twice per week.

The experiment group was administered each time with 5 mg/kg of PTmab bispecific antibody KN026, the reference group was administered each time with 5 mg/kg of Trastuzumab reference sample or Pertuzumab reference sample, and a blank control group was administered with the same volume of PBS buffer.

Figure 23:
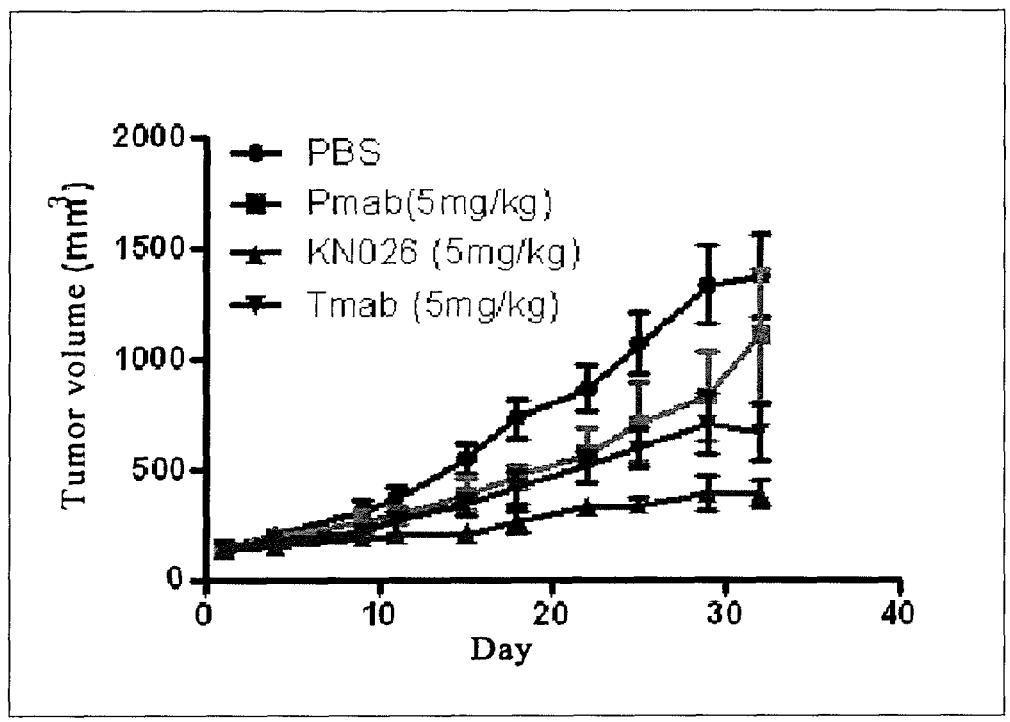
FIG. 23 illustrates influence of a Ptmab bispecific antibody on the tumor size of a human gastric cancer N-87 nude mouse xenograft.

As shown in FIG. 23, comparing to the blank control group, both the experiment group and the reference group showed some tumor inhibition effect on the N-87 nude-mouse xenograft model, wherein the Ptmab bispecific antibody showed a tumor inhibition effect clearly superior to that of the Trastuzumab reference sample alone or the Pertuzumab reference sample alone.

Example 14 Pharmacodynamic Effect of Ptmab Bispecific Antibody on Human Gastric Cancer N-87 Nude-Mouse Xenograft Model Balb/c nude mice were subcutaneously inoculated with human gastric cancer N-87 cells at a dosage of $4 \times 10^6$

TABLE 7

Pharmacokinetic parameters of KN026 and Trastuzumab

| Sample | $t_{1/2}$ h | $T_{max}$ h | $C_{max}$ ug/ml | $AUC_{last}$ h*mg/ml | $AUC_{INF\_obs}$ h*mg/m | $V_d$ ml/kg | $C_1$ ml/h/kg | MRT h |
|---|---|---|---|---|---|---|---|---|
| Ref | 288.15 | 24 | 95.40 | 25.57 | 33.51 | 124.05 | 0.30 | 208.55 |
| KN026 | 259.23 | 8 | 83.63 | 18.48 | 23.33 | 160.29 | 0.43 | 203.23 |

Example 12 Pharmacodynamic Effects of Ptmab Bispecific Antibody on Nude-Mouse Xenograft Model of Human Ovarian Cancer SKOV3

Balb/c nude mice were subcutaneously vaccinated with human ovarian cancer SKOV3 cells at a dosage of $5 \times 10^6$ cells+50% matrigel/mouse, and tumor-bearing mice were grouped randomly with 6 mice in each group (half of them was males and the other half was females). When the tumor was grown to a volume of about 100-150 mm$^3$, a tumor-inhibiting drug was injected by intraperitoneal administration twice each week for two consecutive weeks. The size of cells/mouse, and tumor-bearing mice were grouped randomly with 6 mice in each group (half of them were males and the other half were females). When the tumor grew to a volume of about 100-120 mm$^3$, a tumor-inhibiting drug was injected by IP administration twice each week for three consecutive weeks. The size of tumor was measured twice each week.

2.5 mg/kg of PTmab bispecific antibody KN026 was administered to the experiment group, 2.5 mg/kg of the combination of Trastuzumab reference sample and Pertuzumab reference sample was administered to the reference group each time, and the same volume of PBS buffer was administered to a blank control group each time.

Figure 24:
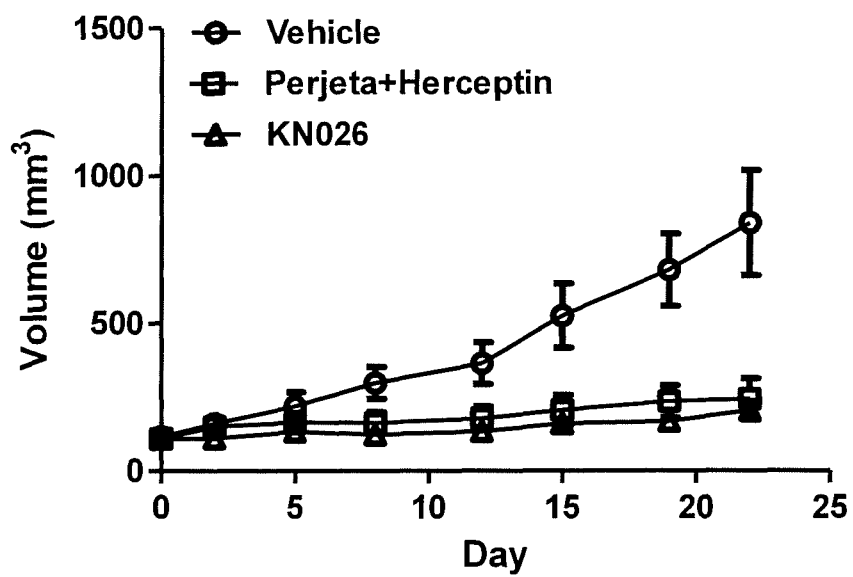
FIG. 24 illustrates influence of a PTmab bispecific antibody on the tumor size of a human gastric cancer N-87 nude mouse xenograft.
Figure 25:
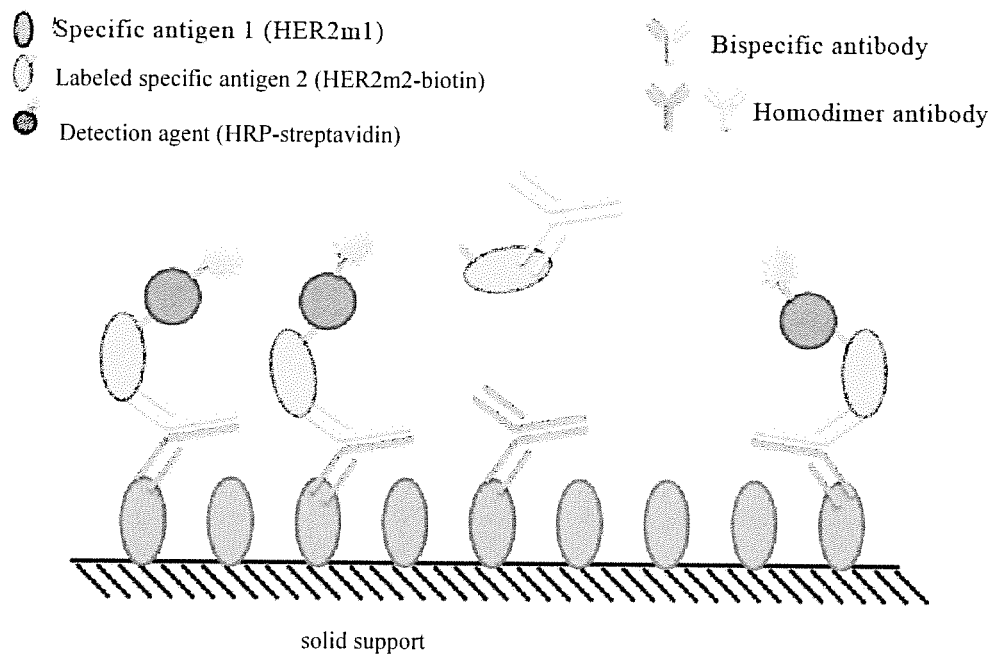
FIG. 25 is a schematic diagram of a method for determining whether or not an antibody is a bispecific antibody and a diagram of a quantification method.
Figure 26:
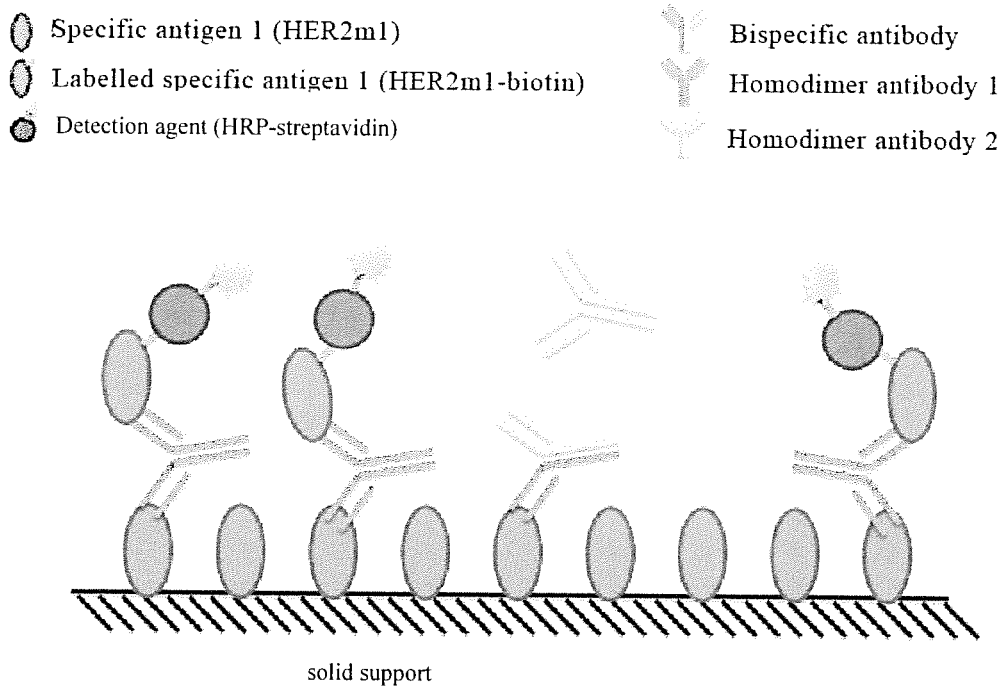
FIG. 26 is a schematic diagram of a method for determining whether or not an antibody mixture comprises a homodimer protein.

As shown in FIG. 24, comparing to the blank control group, both the experiment group and the reference group showed some tumor inhibition effect on the N-87 nude-mouse xenograft model, wherein the PTmab bispecific antibody showed a stronger tumor inhibition effect than the combination of the Trastuzumab reference sample and Pertuzumab reference sample administered in an equal mole.

Example 15 Dosage Dependency of PTmab Bispecific Antibody on HER2 Under-Expression Human Non-Small Cell Lung Cancer NCI-H522 Mouse Xenograft Model NOD/SCID immunodeficiency mice were subcutaneously inoculated with the mixture of non-small cell lung cancer NCI-H522 cells and matrigel (the ratio of the cells to the matrigel was 1:1) to establish the model, the inoculation dosage was $5\times10^6$ cells/mouse, and the tumor-bearing mice were grouped randomly with 6 mice in each group (half of them were males and the other half were females). When the tumor grew to a volume of about 100 mm$^3$, a tumor-inhibiting drug was injected. The day on which IP (intraperitoneal) administration was performed for the first time was labeled as day 0. Then, IP administration was performed once each week for 7 consecutive weeks, and the concentration of the drugs administered was reduced by half (comparing to the concentration used in the first administration). The size of the tumor was measured twice every week.

The experiment group was divided into three sub-groups which were administered with PTmab bispecific antibody KN026 according to the following dosages respectively: 30 mg/kg was administered for the first time, and subsequently, 15 mg/kg was administered each time each week; 10 mg/kg was administered for the first time, and subsequently, 5 mg/kg was administered each time each week; 3 mg/kg was administered for the first time, and subsequently, 1.5 mg/kg was administered each time each week. The blank control group was administered with the same volume of PBS buffer each time.

Figure 27:
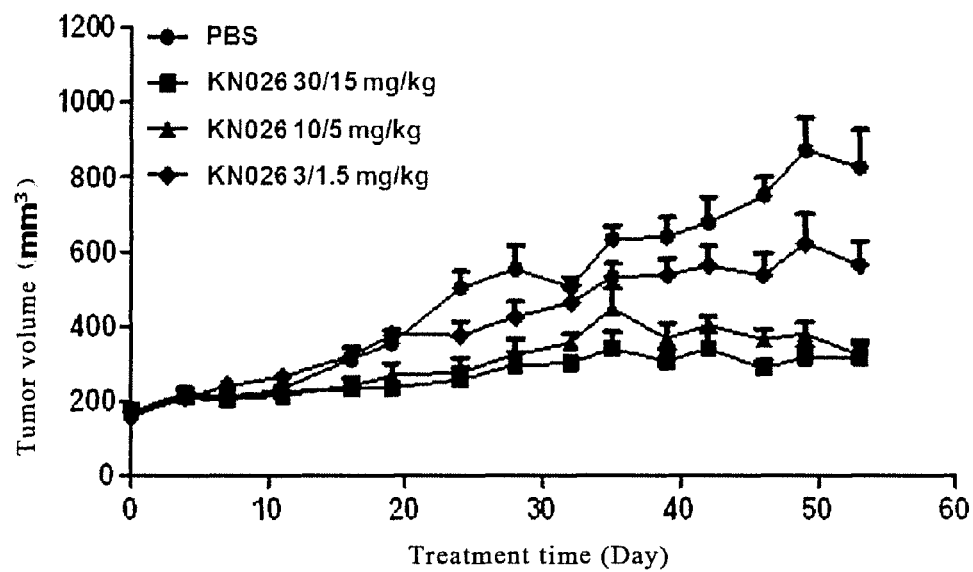
FIG. 27 illustrates dosage dependency of a PTmab bispecific antibody on an HER2 under-expressed human non-small cell lung cancer NCI-H522 mouse xenograft model.

As shown in FIG. 27, comparing to the blank control group, the three experiment groups showed clear tumor inhibiting effects on the NCI-H522 mice xenograft model, and this effect was dosage dependent.

Example 16 Pharmacodynamic Effect of PTmab Bispecific Antibody on HER2 Under-Expression Non-Small Cell Lung Cancer NCI-H522 Mouse Xenograft Model NOD/SCID immunodeficiency mice were subcutaneously inoculated with the mixture of non-small cell lung cancer NCI-H522 cells and matrigel (the ratio of the cells to the matrigel was 1:1) to establish a model, the inoculation dosage was $5\times10^6$ cells/mouse, and the tumor-bearing mice were grouped randomly with 6 mice in each group (half of them were males and the other half were females). When the tumor grew to a volume of about 100 mm$^3$, a tumor-inhibiting drug was injected. The day on which IP (intraperitoneal) administration was performed for the first time was labeled as day 0, and the dosage administered was 5 mg/kg. Then, IP administration was performed once per week and the concentration of the drugs administered was half of that administered in the first time, namely 2.5 mg/kg. IP administration was performed for 7 consecutive weeks. The size of the tumor was measured twice per week.

The experiment group was administered with PTmab bispecific antibody KN026, the reference group was administered with the combination of a Trastuzumab reference sample and a Pertuzumab reference sample, each drug was administered according to the dosage mentioned above, namely 5mgP+5 mgT/kg was administered for the first time, subsequently, 2.5mgP+2.5 mgT/kg was administered each time each week, and the blank control group was administered with the same volume of PBS buffer each time.

Figure 28:
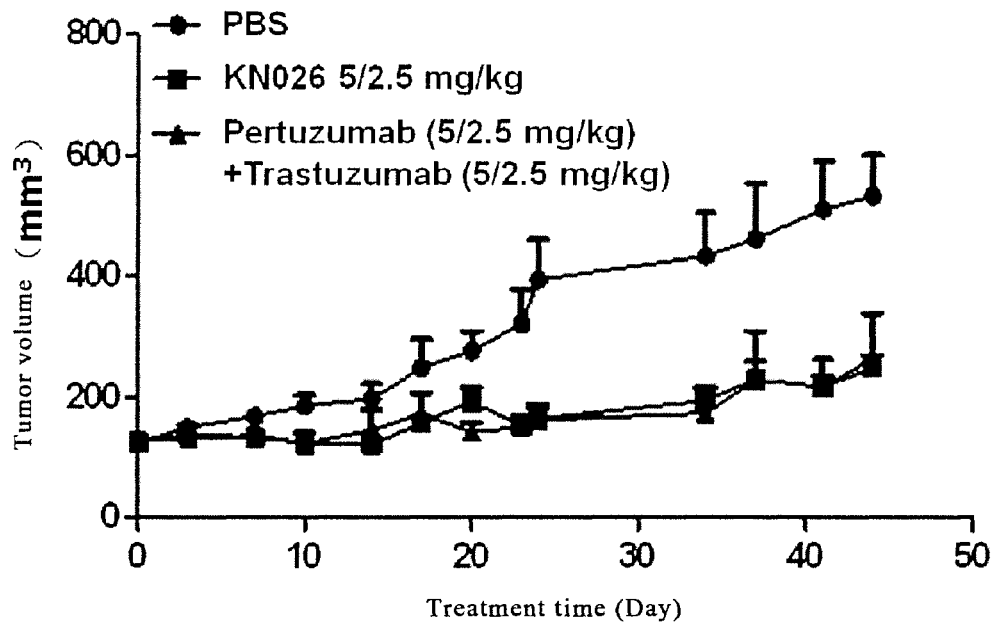
FIG. 28 illustrates that the pharmaceutical effect of a PTmab bispecific antibody on a HER2 under-expressed human non-small cell lung cancer NCI-H522 mouse xenograft model is comparable to that of administering equal mole of Trastuzumab standard sample together with equal mole of Pertuzumab.

As shown in FIG. 28, comparing to the blank control group, both the experiment group and the reference group showed clear tumor inhibiting effect on the NCI-H522 mice xenograft model. Meanwhile, the Ptmab bispecific antibody administered alone had an inhibiting effect comparable to that of the Trastuzumab reference sample and the Pertuzumab reference sample combination.

Although specific embodiments of the present application have been described in detail, it will be understood by those skilled in the art that according to all of the teachings publicly known in the art, various modifications and substitutions of those details may be made, which will be within the scope of the present application. The scopes of the present application are defined by the accompanying claims and any equivalents thereof.

---

The invention claimed is:

1. An isolated anti-HER2 bispecific antibody or an antigen binding portion thereof, said bispecific antibody or antigen binding portion thereof comprising two heavy chains and two identical light chains, wherein:

each of said light chains comprises a variable region having an amino acid sequence selected from the group consisting of amino acid positions 1-107 of SEQ ID NO: 2-SEQ ID NO:4 and SEQ ID NO:6, and one of said two heavy chains comprises a variable region having the amino acid sequence of SEQ ID NO:23; and the other one of said two heavy chains comprises a variable region having the amino acid sequence as set forth in SEQ ID NO: 24.

2. A composition comprising the bispecific antibody or the antigen binding portion thereof of claim 1, and a pharmaceutically acceptable carrier or excipient.

* * * * *